(12) United States Patent
Padget et al.

(10) Patent No.: US 7,686,807 B2
(45) Date of Patent: Mar. 30, 2010

(54) TOOL FOR BONE FIXATION DEVICE

(75) Inventors: Martin Padget, Valencia, CA (US);
Brad S. Culbert, Rancho Santa Margarita, CA (US)

(73) Assignee: Interventional Spine, Inc., Irvine, CA (US)

( * ) Notice: Subject to any disclaimer, the term of this patent is extended or adjusted under 35 U.S.C. 154(b) by 867 days.

(21) Appl. No.: 10/790,670

(22) Filed: Mar. 1, 2004

(65) Prior Publication Data
US 2004/0260297 A1    Dec. 23, 2004

Related U.S. Application Data

(63) Continuation-in-part of application No. 10/440,016, filed on May 16, 2003, now Pat. No. 7,008,428, which is a continuation-in-part of application No. 09/815,263, filed on Mar. 22, 2001, now Pat. No. 6,632,224.

(60) Provisional application No. 60/451,320, filed on Feb. 28, 2003, provisional application No. 60/464,399, filed on Apr. 21, 2003.

(51) Int. Cl.
*A61F 5/00* (2006.01)
(52) U.S. Cl. .................................. 606/86 R
(58) Field of Classification Search ............ 606/72, 606/103, 105, 104, 281, 282, 291, 300, 301, 606/324, 86 R, 86 A
See application file for complete search history.

(56) References Cited

U.S. PATENT DOCUMENTS 2,243,717 A * 5/1941 Moreira ................. 606/65

(Continued)

FOREIGN PATENT DOCUMENTS

DE    198 32 798 C1    11/1999

(Continued)

OTHER PUBLICATIONS

Supplementary International Search Report received in co-pending European Appl. No. 04716129.4, mailed Apr. 22, 2008.

(Continued)

*Primary Examiner*—Thomas C Barrett
*Assistant Examiner*—Michael J Araj
(74) *Attorney, Agent, or Firm*—Knobbe, Martens, Olson & Bear LLP

(57) ABSTRACT

A tool for inserting a bone fixation device is provided. The tool generally includes an elongate outer body and an elongate inner body, each having a proximal end, a distal end, and a longitudinal axis. The tool typically includes a pin-receiving portion at the distal end of the outer body for receiving a proximal pin of a bone fixation device. The tool may further include first and second levers pivotally mounted to the inner member at respective pivot axes, and each of the levers having a gripping portion. The levers preferably include finger engagement portions, wire-gripping portions, and are preferably configured to be axially movable relative to the outer body. The levers are generally configured such that a proximal force on the finger engagement portions relative to the outer body will cause the pin engagement portions to close and to move proximally such that a guidewire of a bone fixation device placed between the wire-gripping portions may be gripped and pulled proximally.

19 Claims, 17 Drawing Sheets

U.S. PATENT DOCUMENTS

| | | | |
|---|---|---|---|
| 5,234,431 A | | 8/1993 | Keller |
| 5,312,410 A | | 5/1994 | Miller et al. |
| 5,449,361 A | | 9/1995 | Preissman |
| 5,649,931 A | | 7/1997 | Bryant et al. |
| 5,720,753 A | * | 2/1998 | Sander et al. ............... 606/104 |
| 5,810,821 A | | 9/1998 | Vandewalle |
| 5,893,850 A | * | 4/1999 | Cachia ........................ 606/72 |
| 5,993,459 A | | 11/1999 | Larsen et al. |
| 6,022,352 A | | 2/2000 | Vandewalle |
| 6,066,142 A | | 5/2000 | Serbousek et al. |
| 6,068,648 A | | 5/2000 | Cole et al. |
| 6,251,111 B1 | * | 6/2001 | Barker et al. ................. 606/61 |
| 6,267,767 B1 | | 7/2001 | Strobel et al. |
| 6,290,701 B1 | * | 9/2001 | Enayati ........................ 606/72 |
| 6,379,363 B1 | | 4/2002 | Herrington et al. |
| 6,488,693 B2 | | 12/2002 | Gannoe et al. |
| 6,520,907 B1 | | 2/2003 | Foley et al. |
| 6,579,293 B1 | | 6/2003 | Chandran |
| 6,582,453 B1 | | 6/2003 | Tran et al. |
| 6,585,730 B1 | | 7/2003 | Foerster |
| 6,585,740 B2 | | 7/2003 | Schlapfer |
| 6,589,249 B2 | | 7/2003 | Sater et al. |
| 6,599,297 B1 | | 7/2003 | Carlsson et al. |
| 6,632,224 B2 | | 10/2003 | Cachia et al. |
| 6,890,333 B2 | | 5/2005 | von Hoffmann et al. |
| 6,908,465 B2 | | 6/2005 | von Hoffmann et al. |
| 6,929,606 B2 | | 8/2005 | Ritland |
| 7,326,211 B2 | | 2/2008 | Padget et al. |
| 2001/0027320 A1 | | 10/2001 | Sasso |
| 2008/0097436 A1 | | 4/2008 | Culbert et al. |
| 2008/0108996 A1 | | 5/2008 | Padget et al. |

FOREIGN PATENT DOCUMENTS

| | | |
|---|---|---|
| EP | 0 625 336 A | 11/1994 |
| JP | 6-319742 A | 11/1994 |
| WO | WO 99/62417 | 12/1999 |
| WO | WO 00/67652 | 5/2000 |
| WO | WO 03/043488 | 5/2003 |
| WO | WO 2004/008949 | 1/2004 |
| WO | WO 2004/078220 | 9/2004 |
| WO | WO 2004/078221 | 9/2004 |
| WO | WO 2007/124130 | 11/2007 |

OTHER PUBLICATIONS

Examination Report received in corresponding Australian Appl. No. 2004218498, mailed Nov. 25, 2008, 3 pages.

Written Opinion of the International Searching Authority received in corresponding PCT Appl. No. PCT/US04/006125, mailed Nov. 16, 2004, 4 pages.

International Preliminary Report on Patentability received in corresponding PCT Appl. No. PCT/US04/006125, mailed Sep. 15, 2005, 2 pages.

Official Action received in corresponding European Appl. No. 04716129.4, mailed Oct. 10, 2008.

Second Official Action received in corresponding European Appl. No. 04716129.4, mailed Mar. 2, 2009, 4 pages.

* cited by examiner

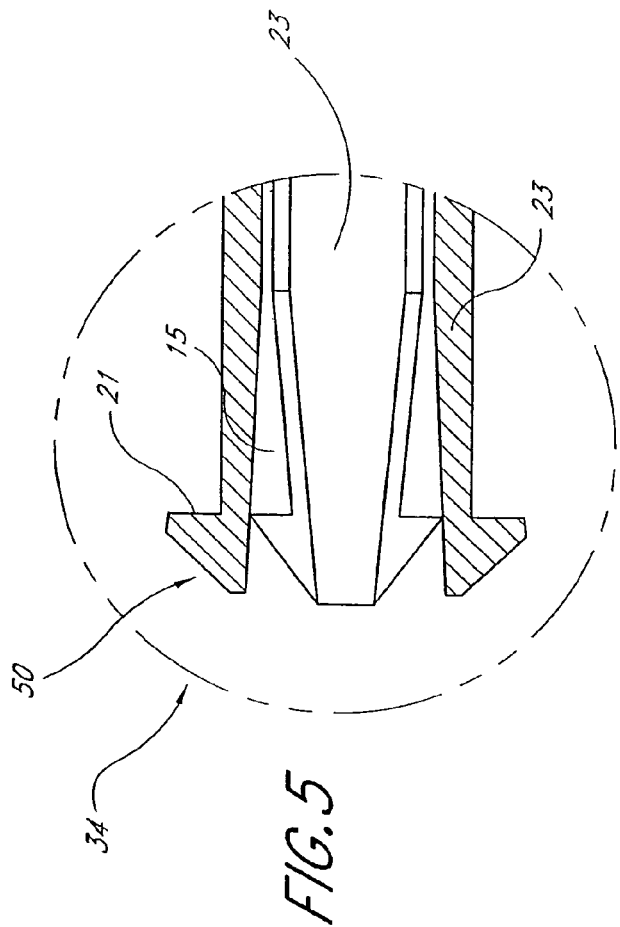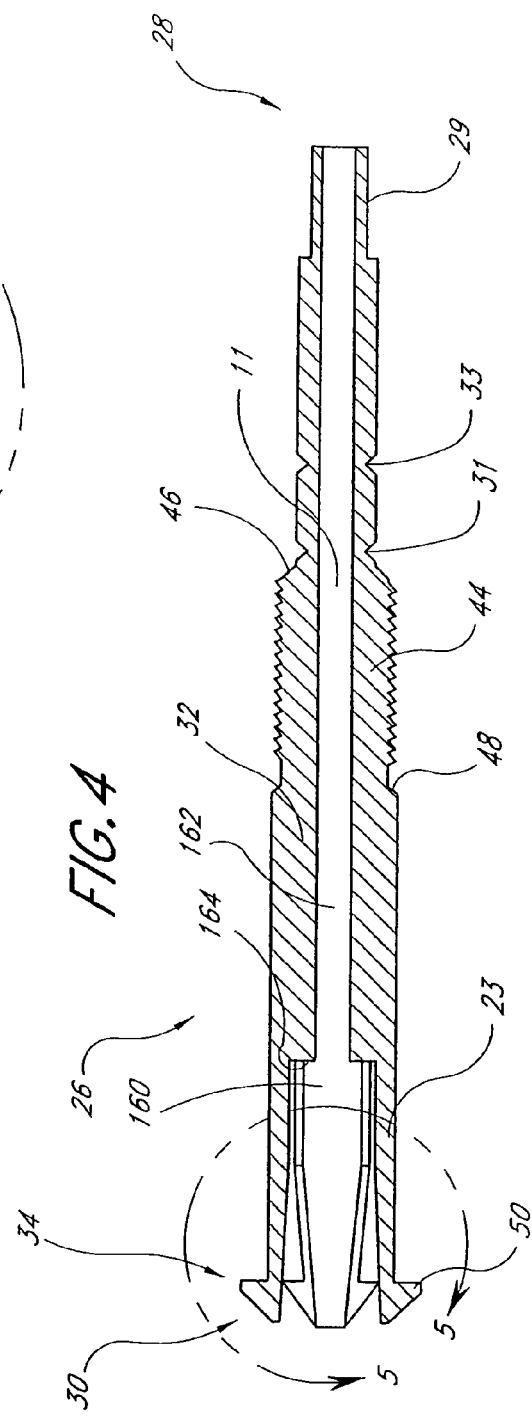

TOOL FOR BONE FIXATION DEVICE

RELATED APPLICATION

This application is a continuation-in-part of U.S. patent application Ser. No. 10/440,016, filed May 16, 2003, now U.S. Pat. No. 7,008,428 which is a continuation of U.S. patent application Ser. No. 09/815,263 filed Mar. 22, 2001 now U.S. Pat. No. 6,632,224, issued Oct. 14, 2003 and claims priority benefit under 35 U.S.C. § 119(e) of Provisional Application 60/451,320 filed Feb. 28, 2003 and Provisional Application 60/464,399 filed Apr. 21, 2003, both of which are hereby incorporated by reference in their entirety.

BACKGROUND

1. Field of the Invention

The invention relates in general to the field of bone fixation devices, and more specifically to an insertion tool for a bone fixation device.

2. Description of the Related Art

Bones which have been fractured, either by accident or severed by surgical procedure, must be kept together for lengthy periods of time in order to permit the rectification and bonding of the severed parts. Accordingly, adjoining parts of a severed or fractured bone are typically clamped together or attached to one another by means of a pin or a screw driven through the rejoined parts. Movement of the pertinent part of the body may then be kept at a minimum, such as by application of a cast, brace, splint, or other conventional technique, in order to promote healing and avoid mechanical stresses that may cause the bone parts to separate during bodily activity.

The surgical procedure of attaching two or more parts of a bone with a pin-like device requires an incision into the tissue surrounding the bone and the drilling of a hole through the bone parts to be joined. Due to the significant variation in bone size, configuration, and load requirements, a wide variety of bone fixation devices have been developed in the prior art. In general, the current standard of care relies upon a variety of metal wires, screws, and clamps to stabilize the bone fragments during the healing process. Following a sufficient bone healing period of time, the percutaneous access site or other site may require re-opening to permit removal of the bone fixation device.

Long bone fractures are among the most common encountered in the human skeleton. Many of these fractures and those of small bones and small bone fragments must be treated by internal and external fixation methods in order to achieve good anatomical position, early mobilization, and early and complete rehabilitation of the injured patient.

The internal fixation techniques commonly followed today frequently rely upon the use of Kirschner wires (K-wires), intramedullary pins, wiring, plates, screws, and combinations of the foregoing. The particular device or combination of devices is selected to achieve the best anatomic and functional condition of the traumatized bone with the simplest operative procedure and with a minimal use of foreign-implanted stabilizing material. A variety of alternate bone fixation devices are also known in the art, such as, for example, those disclosed in U.S. Pat. No. 4,688,561 to Reese, U.S. Pat. No. 4,790,304 to Rosenberg, and U.S. Pat. No. 5,370,646 to Reese, et al.

Notwithstanding the common use of the K-wire to achieve shear-force stabilization of bone fractures, K-wire fixation is attended by certain known risks. For example, a second surgical procedure is required to remove the device after healing is complete. Removal is recommended, because otherwise the bone adjacent to an implant becomes vulnerable to stress shielding as a result of the differences in the modulus of elasticity and density between metal and the bone.

In addition, an implanted K-wire may provide a site for a variety of complications ranging from pin-tract infections to abscesses, resistant osteomyelitis, septic arthritis, and infected nonunion.

Another potential complication involving the use of K-wires is in vivo migration. Axial migration of K-wires has been reported to range from 0 mm to 20 mm, which can both increase the difficulty of pin removal as well as inflict trauma to adjacent tissue.

As conventionally utilized for bone injuries of the hand and foot, K-wires project through the skin. In addition to the undesirable appearance, percutaneously extending K-wires can be disrupted or cause damage to adjacent structures such as tendons if the K-wire comes into contact with external objects.

Notwithstanding the variety of bone fasteners that have been developed in the prior art, there remains a need for a bone fastener of the type that can accomplish shear-force stabilization with minimal trauma to the surrounding tissue both during installation and following bone healing.

In addition, there remains a need for a simple, easy to use tool for inserting and anchoring a bone fixation device while causing minimal trauma to the surrounding tissue during installation.

SUMMARY

Thus, in one embodiment, a method of fixing a first piece of bone to a second piece of bone comprises providing a pin having at least one laterally moveable distal anchor and a lumen extending therethrough. The distal anchor is inserted through the first piece of bone and into the second piece of bone while the distal anchor is permitted to move laterally inwardly as needed. A deployment tool grips a proximal portion of a wire that extends axially through the lumen. The deployment tool moves the wire axially through the lumen such that a distal portion of the wire resists radial inward deflection of the distal anchor, thereby locking the distal anchor with respect to lateral inward movement.

In another embodiment, a tool for inserting a bone fixation device is provided. The tool includes an outer body and an inner body, each having a proximal end, a distal end, and a longitudinal axis. The tool also includes a pin-receiving portion at the distal end of the outer body for receiving a proximal pin of a bone fixation device. The tool further includes first and second levers pivotally mounted to the inner member at respective pivot axes, and each of the levers having a gripping portion.

In another embodiment, a tool is provided which comprises body having a proximal end and a distal end. The tool further includes at least one finger grip portion, a pin-gripping portion at the distal end of the body. The tool is configured such that proximal movement of the at least one finger grip portion causes a guidewire of a bone fixation device to be gripped and moved proximally with respect to a pin of the bone fixation device.

In another embodiment of a tool for deploying a bone fixation device, the tool comprises a longitudinal tubular outer body having a proximal end, a distal end, and at least one longitudinal slot in the outer body. The tool also includes a longitudinal inner body slidably and concentrically disposed within the outer body, and at least one lever pivotally mounted to a distal portion of the inner body. The lever preferably includes a finger engagement portion, a wire-gripping portion, and is preferably configured to be axially movable within the slot. The lever is preferably configured such that a proximal force on the finger engagement portion relative to the outer body will cause the pin engagement portion to close and to move proximally.

In yet another embodiment, a bone fixation system is disclosed which includes a bone fixation device and an insertion tool. The bone fixation device comprises: a first elongate tubular body, having a proximal end, a distal end and a longitudinal axis. A distal anchor is on the fixation device, movable from a low profile orientation for distal insertion through a bore in the bone to an inclined orientation to resist axial proximal movement through the bore. An elongate pin is axially movable within the tubular body and associated with the anchor, such that proximal retraction of the pin with respect to the tubular body advances the distal anchor from the axial orientation to the inclined orientation. The device also includes a second elongate tubular body, having a proximal end, a distal end, and a longitudinal axis. At least one retention structure lies in between the second elongate tubular body and the elongate pin. The retention structure permits proximal movement of the elongate pin with respect to the second elongate tubular body but resists distal movement of the pin with respect to the second elongate tubular body. The first tubular body may be used to deploy the distal anchor, and may then be removed and replaced by the second tubular body. The second tubular body cooperates with the pin to apply compression to the bone. The system also includes an insertion device comprising an elongate body having a proximal end, a distal end, and a central axis. The insertion device also includes a pair of levers configured to be pivotally and axially movable relative to the body. The levers preferably have finger engagement portions and pin engagement portions. The insertion device is preferably configured such that a force applied to the finger engagement portions causes the levers to be engaged on the pin of the fixation device, and causes the pin to be proximally retracted.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the present invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF DRAWINGS

Having thus summarized the general nature of the invention, certain preferred embodiments and modifications thereof will become apparent to those skilled in the art from the detailed description herein having reference to the figures that follow, of which:

FIG. 4 is a longitudinal cross-sectional view through the pin body of FIG. 2;

FIG. 5 is an enlarged detail view of the distal end of the device shown in FIG. 4;

DETAILED DESCRIPTION

Figure 1:
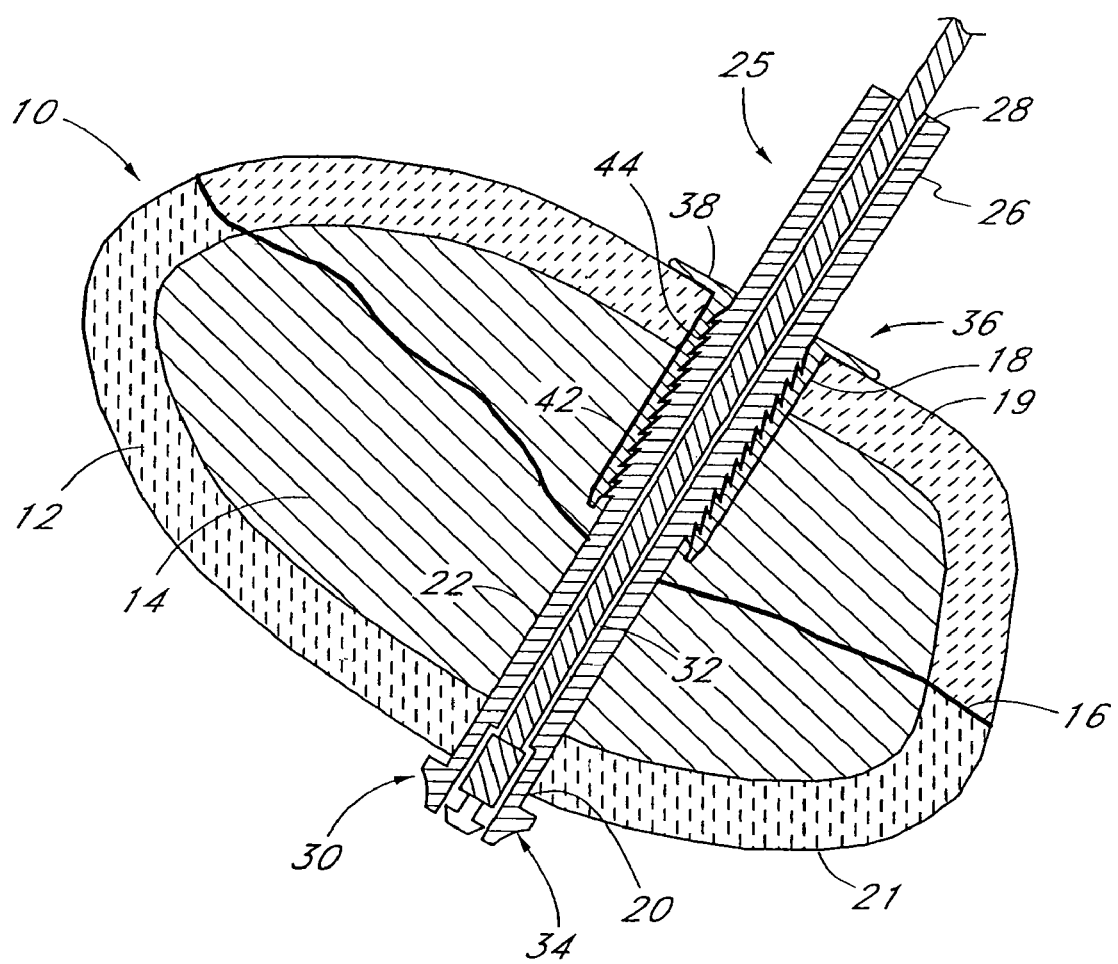
FIG. 1 is a schematic section view of a bone fixation device positioned within a fractured bone.

Although the application of the various embodiments will be disclosed in connection with the simplified bone fracture of FIG. 1, the methods and structures disclosed herein are intended for application in any of a wide variety of bones and fractures, as will be apparent to those of skill in the art in view of the disclosure herein. For example, the bone fixation device can be applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures and osteotomies and arthrodesis of the tarsal bones such as the calcaneus and talus may also be treated. Spiked washers can be used, attached to the collar or freely movable beneath the collar. The bone fixation device may be used with or without plate(s) or washer(s), all of which can be either permanent, absorbable or comprising both.

Fractures of the fibular and tibial malleoli, pilon fractures and other fractures of the bones of the leg can be fixated and stabilized with or without the use of plates, both absorbable or non-absorbing types, and with alternate disclosed embodiments. One example is the fixation of the medial malleolar avulsion fragment fixation with the radially and axially expanding compression device. Each of the foregoing may be treated in accordance with the present invention, by advancing one of the fixation devices disclosed herein through a first bone component, across the fracture, and into the second bone component to fix the fracture.

To assist in the description of the disclosed embodiment, words such as upward, upper, downward, lower, vertical, horizontal, inward, outward, proximal, and distal are used to describe the accompanying figures. The term "axial" as used herein refers to the axis of a body or structure and therefore can be substantially synonymous with the term "longitudinal" as used herein. It will be appreciated, however, that the illustrated embodiments can be located or oriented in a variety of desired positions.

Referring to FIG. 1, there is illustrated generally a bone 10, shown in cross-section to reveal an outer cortical bone component 12 and an inner cancellous bone component 14. A fracture 16 is schematically illustrated as running through the bone to at least partially divide the bone 10 into what will for the present purposes be considered a proximal component 19 and a distal component 21. The fracture is simplified for the purpose of illustrating the application of the disclosed embodiments. However, as will be understood by those skilled in the art, the fracture 16 may extend through the bone at any of a wide variety of angles, depths, and sizes.

Figure 2:
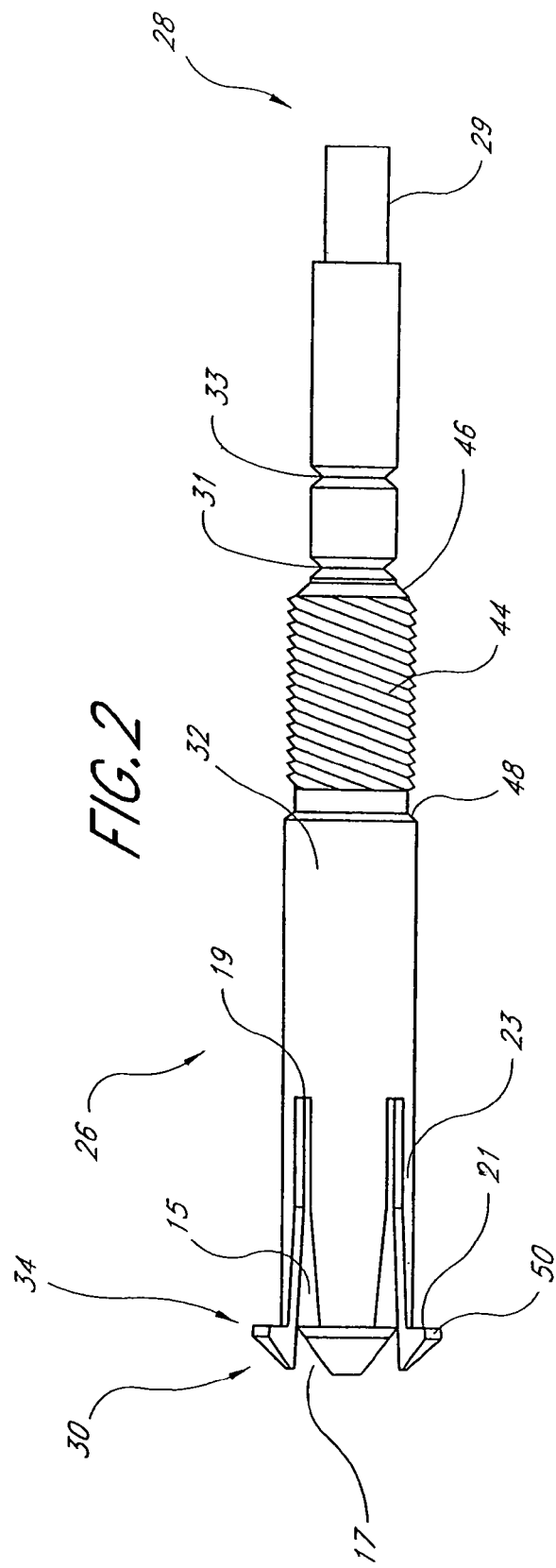
FIG. 2 is a side elevational view of an alternate embodiment of a pin body in accordance with the present invention.

Referring to FIGS. 2-9, there is illustrated an embodiment of a fixation device having presently desirable features and advantages. This embodiment is optimized for construction from a metal, such as titanium or titanium alloy, although other materials including those disclosed elsewhere herein may be utilized for the present embodiment. Referring to FIGS. 2 and 4, the fixation device includes a body 32 which is in the form of a pin 26 extending between a proximal end 28 and a distal end 30. The distal end 30 includes a plurality of friction enhancing or interference fit structures such as ramped extensions or barbs 50, for engaging the distal cortical bone or other surface or interior cancellous bone.

Although the illustrated embodiment includes four barbs 50, oriented at 90° with respect to each other, anywhere from one to about twelve or more barbs 50 may be utilized as will be apparent to those of skill in the art in view of the disclosure herein. The barbs 50 may be radially symmetrically distributed about the longitudinal axis of the pin 26. Each barb 50 is provided with a transverse engagement surface 21, for contacting the distal surface of the cortical bone or other structure or surface against which the barb 50 is to anchor. Transverse engagement surfaces 21 may lie on a plane which is transverse to the longitudinal axis of the pin 26, or may be inclined with respect to the longitudinal axis of the pin 26.

Each of the transverse engagement surfaces 21 in the illustrated embodiment lies on a common plane which is transverse to the longitudinal axis of the pin 26. Two or more planes containing engagement surfaces 21 may alternatively be provided. The transverse engagement surfaces 21 may also lie on one or more planes which are non-normal to the longitudinal axis of pin 26. For example, the plane of a plurality of transverse engagement surfaces 21 may be inclined at an angle within the range of from about 35° or 45° to about 90° with respect to the longitudinal axis of the pin 26. The plane of the transverse engagement surface may thus be selected to take into account the angle of the distal surface of the bone through which the pin may be positioned, as may be desired in certain clinical applications.

In order to facilitate the radially inward compression of the barbs 50 during the implantation process, followed by radially outward movement of the barbs 50 to engage the distal bone surface, each barb 50 in the illustrated embodiment is carried by a flexible or hinged lever arm 23. Lever arms 23 may be formed by creating a plurality of axial slots 15 in the sidewall of the pin 26. The axial slots 15 cooperate with a central lumen 11 to isolate each barb 50 on a corresponding lever arm 23. The axial length of the axial slots 15 may be varied depending upon various desired physical characteristics, such as the desired length over which flexing is distributed, the range of lateral motion, and upon the desired construction material. For a relatively rigid material such as titanium, axial lengths of the axial slot 15 in excess of about 0.1 inches and preferably in excess of about 0.2 inches are utilized on a pin 26 having an outside diameter of about 0.1 inches and a length of about 1.25 inches. Axial slots 15 will generally extend within a range of from about 5% to about 90%, and often within about 10% to about 30% of the overall length of the pin 26.

With continued reference to FIGS. 2, 4, 5 and 9, the circumferential width of the slots 15 at the distal end 30 is selected to cooperate with the dimensions of the barbs 50 to permit radial inward deflection of each of the barbs 50 so that the pin 26 may be press fit through a predrilled hole having an inside diameter approximately equal to the outside diameter of the pin 26 just proximal to the transverse engagement surfaces 21. For this purpose, at least a portion of each of the slots 15 tapers in circumferential direction width from a relatively larger dimension at the distal end 30 to a relatively smaller dimension at the proximal limit of the axial slot 15, as shown in FIG. 2. In the illustrated embodiment, each slot 15 has a width of about 0.20 inches at the proximal end and a width of about 0.035 inches at the distal end in the unstressed orientation. The width of the slot 15 may taper continuously along its length, or, as in the illustrated embodiment, is substantially constant for a proximal section and tapered over a distal section of the slot 15. The wall thickness of the lever arm 23 may also be tapered to increase the diameter of the central lumen 11 in the distal direction. This will allow a reduced compressed crossing profile before the inside surfaces of the lever arms bottom out against each other.

The pin 26 is additionally provided with a plurality of retention structures 44 for engaging with a proximal anchor 36. Relative rotational movement between the pin 26 and the proximal anchor 36 can result in relative axial movement between the pin 26 and the proximal anchor 36

Figure 7:
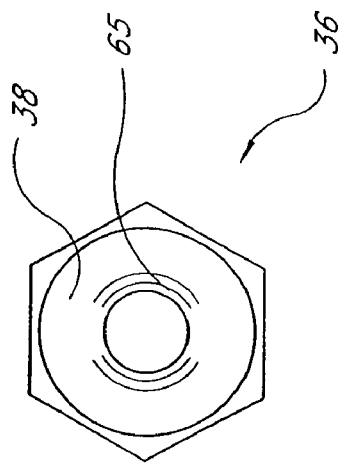
FIG. 7 is a proximal end elevational view of the proximal anchor of FIG. 6.

The retention structures 44 are configured to engage with the proximal anchor 36. In one embodiment, the retention structures 44 are spaced apart axially along the pin 26 between a proximal limit 46 and a distal limit 48. The axial distance between proximal limit 46 and distal limit 48 is related to the desired axial travel of the proximal anchor 36, and thus the range of functional sizes of the pin. In one embodiment of the pin 26, the retention structures 44 comprise a plurality of threads, adapted to cooperate with the complimentary retention structures 42 on the proximal anchor 36, which may be a complimentary plurality of threads. In this embodiment, the proximal anchor 36 may be distally advanced along the pin 26 by rotation of the proximal anchor 36 with respect to the pin 26. Proximal anchor 36 may advantageously be removed from the pin 26 by reverse rotation to permit removal of the pin 26 from the patient. For this purpose, collar 38 is preferably provided with a gripping configuration or structure to permit a removal tool to rotate collar 38 with respect to the pin 26. Any of a variety of gripping surfaces may be provided, such as one or more slots, flats, bores, or the like. In the illustrated embodiment, the collar 38 is provided with a polygonal, and in particular, a hexagonal circumference, as seen in FIG. 7.

Figure 3:
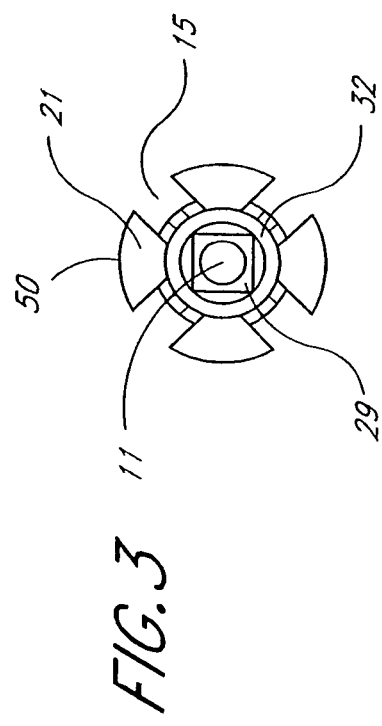
FIG. 3 is a distal end elevational view of the pin body of FIG. 2.

The proximal end 28 of the pin 26 is similarly provided with a structure 29 for permitting rotational engagement with an installation or a removal tool. Rotational engagement may be accomplished using any of a variety of shapes or configurations, as will be apparent to those of skill in the art. One convenient structure is to provide the proximal end 28 with one or more flat side walls, for rotationally engaging a complimentary structure on the corresponding tool. As illustrated in FIG. 3, the proximal end 28 may be provided with the structure 29 having a square cross-section. Alternatively, the exterior cross-section through proximal end 28 may be any of a variety of configurations to permit rotational coupling, such as triangular, hexagonal, or other polygons, or one or more axially extending flat sides or channels on an otherwise round body.

The foregoing structures enable the use of an installation and/or deployment tool having a concentric core within a sleeve configuration in which a first component (e.g. a sleeve) engages the proximal anchor 36 (see FIGS. 6 and 7) and a second component (e.g. a core) engages the proximal rotational engagement structure 29 of pin 26. The first component may be rotated with respect to the second component, so that the proximal anchor 36 may be rotated onto or off of the retention structures 44 on pin 26. In a modified arrangement, a first tool (e.g., a pair of pliers or a wrench) may be used to engage the proximal anchor 36 and a second tool (e.g., a pair of pliers or a wrench) may be used to engage the proximal rotational engagement structure 29 of pin 26. In such an arrangement, the first tool may be rotated with respect to the second tool (or vice versa), so that the proximal anchor 36 may be rotated onto or off the retention structures 44 on the pin 26.

Alternatively, the retention structures 42 on the proximal anchor 36 may be toleranced to permit distal axial advancement onto the pin 26, such as by elastic deformation, but require rotation with respect to the pin 26 in order to remove the proximal anchor 36 from the pin 26.

Any of a variety of alternative retention structures may be configured, to permit removal of the proximal anchor 36 preferably after implantation and a bone healing period of time. For example, the retention structures 44 can be threads with a plurality of axially extending flats or interruptions. These threads can correspond with a plurality of axial flats on the retention structures 42 of the proximal anchor 36. This configuration enables a partial rotation (e.g., 90°) of the proximal anchor 36 with respect to the pin 26 to disengage the retention structures 42, 44 and permit axial withdrawal of the proximal anchor 36 from the pin 26. One or both of the retention structures 42 and 44 may comprise a helical thread or one or more circumferentially extending ridges or grooves. In one embodiment, the retention structures 42, 44 can have a pitch to achieve the desired axial movement based on relative rotational movement between the pin 26 and the proximal anchor 36. The threads of the retention structures 42, 44 can have a fine pitch to a course pitch. For example, a fine pitch may be selected where a number of rotations of proximal anchor 36 is desired to produce a relatively small axial travel of the anchor 36 with respect to the pin 26. In this configuration, relatively high compressive force can be achieved between the proximal anchor 36 and the distal anchor 34. This configuration will also provide a relatively high resistance to inadvertent reverse rotation of the proximal anchor 36. In another embodiment, the threads of the retention structures 42, 44 have a relatively course pitch, such as might be found on a luer connector. These threads can provide quick twist connection for rapid relative axial movement of between the pin 26 and the proximal anchor 36. A relatively low number of rotations or partial rotation of the proximal anchor 36 provides a significant axial travel with respect to the pin 26. This configuration may enhance the tactile feedback with respect to the degree of compression placed upon the bone. The thread pitch or other characteristics of the corresponding retention structures can be optimized through routine experimentation by those of skill in art in view of the disclosure herein, taking into account the desired clinical performance.

With reference to FIG. 4, the pin 26 can have a break point to facilitate breaking and removal of a proximal portion of the pin 26. The break point can be located proximal the proximal anchor 36 when the proximal anchor 36 is threadably coupled to the pin 26.

In one embodiment, at least a first break point 31 can be a portion of the pin 26 with a reduced wall thickness. That is, the break point 31 of the pin 26 can have a cross-sectional area less than the cross-sectional area of other portions of the pin 26. The proximal portion of the pin 26 which projects proximally of the collar 38 following tensioning of the fixation system. Break point 31 in the illustrated embodiment comprises an annular recess or groove, which provides a designed failure point if lateral force is applied to the proximal end 28 while the remainder of the attachment system is relatively securely fixed. At least a second break point 33 may also be provided, depending upon the axial range of travel of the proximal anchor 36 with respect to the pin 26.

In one embodiment having two or more break points 31, 33, the distal break point 31 is provided with one or more perforations or a deeper recess than the proximal break point 33. In this manner, the distal break point 31 will preferentially fail before the proximal break point 33 in response to lateral pressure on the proximal end 28. This will ensure the minimum projection of the pin 26 beyond the collar 38 following deployment and severing of the proximal end 28 as will be appreciated in view of the disclosure herein.

Figure 6:
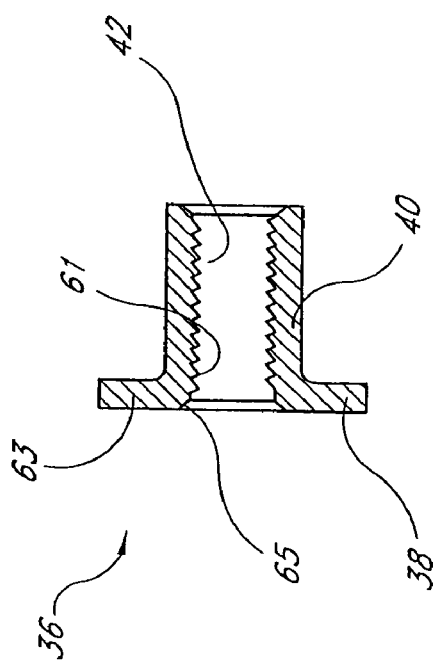
FIG. 6 is a cross-sectional view through a proximal anchor for use with the pin body of FIG. 2.

Proximal projection of the proximal end 28 from the proximal anchor 36 following implantation and breaking at a breakpoint 31 may additionally be minimized or eliminated by allowing the breakpoint 31 or 33 to break off within the proximal anchor 36. Referring to FIG. 6, the retention structure 42 may terminate at a point 61 distal to a proximal surface 63 on the anchor 36. An inclined or tapered annular surface 65 increases the inside diameter of the central aperture through proximal anchor 36, in the proximal direction. After the proximal anchor 36 has been distally advanced over a pin 26, such that a breakpoint 31 is positioned between the proximal limit 61 and the proximal surface 63, lateral pressure on the proximal end 28 of pin 26 will allow the breakpoint 31 to break within the area of the inclined surface 65. In this manner, the proximal end of the pin 26 following breaking resides at or distally of the proximal surface 63, thus minimizing the profile of the device and potential tissue irritation.

For any of the axially deployable embodiments disclosed above, installation can be simplified through the use of an installation tool. The installation tool may comprise a pistol grip, a syringe-type grip, or plier-type grip so that the clinician can position the tool at the proximal extension of pin 32 and through one or more contractions with the hand, the proximal anchor 36, 52 and distal anchor 34 can be drawn together to appropriately tension against the bone fragments. The use of a precalibrated tool can permit the application of a predetermined tension in a uniform manner from pin to pin.

Calibration of the installation device to set a predetermined load on the pin can be accomplished through any of a variety of means which will be understood to those of skill in the art. For example, the pin 32 may be provided with one or more score lines or transverse bores or other modifications which limit the tensile strength of the part at one or more predetermined locations. In this manner, axial tension applied to the proximal end 28 with respect to the collar 54 will apply a predetermined load to the bone before the pin 32 will separate at the score line. Alternatively, internal structures within the installation tool can be provided to apply tension up to a predetermined limit and then release tension from the distal end of the tool.

Figure 8:
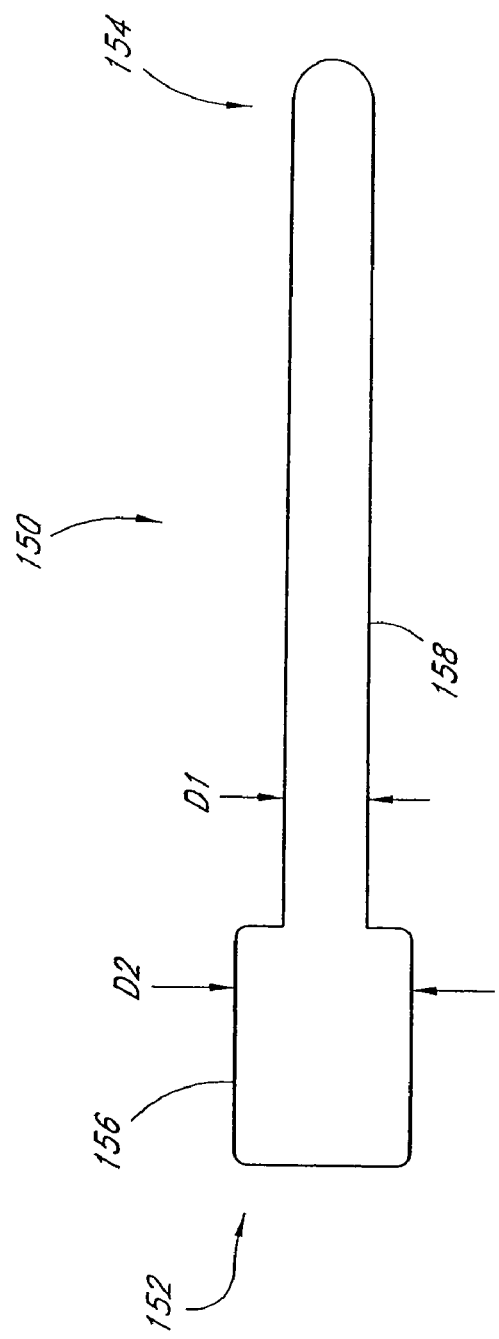
FIG. 8 is a side elevational view of a guide wire that may be used with the pin body of FIG. 2.
Figure 9:
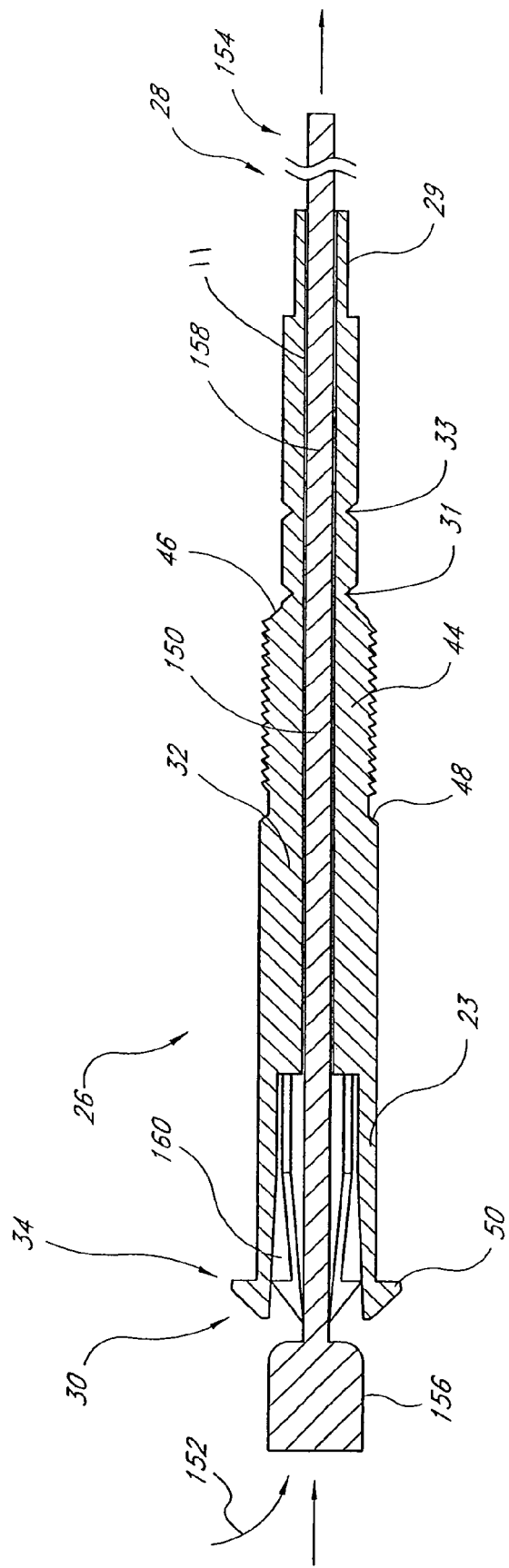
FIG. 9 is a longitudinal cross-sectional view of the guide wire of FIG. 8 and the pin body of FIG. 2.

FIG. 8 illustrates a locking guide wire 150 that may be used with the fixation device 25 described above. The guide wire has a distal end 152 and a proximal end 154. The illustrated guide wire 150 comprises a locking portion 156 that is located at the distal end 152 of the guide wire 150 and an elongated portion 158 that preferably extends from the distal portion 156 to the proximal end 154 of the guide wire 150. The diameter D1 of the elongated portion 158 is generally smaller than the diameter D2 of the distal portion 154. The guide wire 150 can be made from stainless steel, titanium, or any other suitable material. Preferably, in all metal systems, the guide wire 150 and locking portion 156 are made from the same material as the remainder of the fixation device 25 to prevent cathodic reactions.

The locking portion 156 on guide wire 150 can take any of a variety of forms, and accomplish the intended function as will be apparent to those of skill in the art in view of the disclosure herein. For example, a generally cylindrical locking structure, as illustrated, may be used. Alternatively, any of a variety of other configurations in which the cross section is greater than the cross section of the proximal portion 158 may be used. Conical, spherical, or other shapes may be utilized, depending upon the degree of compression desired and the manner in which the locking portion 156 is designed to interfit with the distal end 30 of the pin.

The guide wire 150 is configured such that its proximal end can be inserted through the lumen 11 of the pin 26. With reference to FIG. 4, the lumen 11 preferably comprises a first portion 160 and a second portion 162. The first portion 160 is generally located at the distal end 30 within the region of the lever arms of the pin 26. The second portion 162 preferably extends from the first portion 160 to the proximal end 28 of the pin 26. The inside diameter of the first portion 160 is generally larger than the diameter of the second portion 162. As such, the junction between the first portion 160 and the second portion 162 forms a transverse annular engagement surface 164, which lies transverse to the longitudinal axis of the pin 26.

As mentioned above, the guide wire 150 is configured such that its proximal end can be inserted through the lumen 11 of the pin 26. As such, the diameter D1 of the elongated portion 158 is less than the diameter of the second portion 162 of the lumen 11. In contrast, the diameter D2 of distal portion 156 is generally equal to or larger than the diameter of the first portion 160 and larger than the diameter of the second portion 162. This arrangement allows the distal portion 156 to be retracted proximally into the first portion 160 but prevents the distal portion 156 from passing proximally through the pin 26. In embodiments in which the distal portion 156 is larger than the diameter of the first portion 160, the first portion may expand the distal anchor 34 beyond its relaxed diameter.

In addition, any of a variety of friction enhancing surfaces or surface structures may be provided, to resist distal migration of the locking guide wire 150, post deployment. For example, any of a variety of radially inwardly or radially outwardly directed surface structures may be provided along the length of the locking guide wire 150, to cooperate with a corresponding surface structure on the inside surface of the lumen 11, to removal retain the locking guide wire 150 therein. In one embodiment, a cylindrical groove or ridge is provided on the inside surface of the lumen 11 to cooperate with a radially outwardly extending annular flange or groove on the outside diameter of the locking guide wire 150. The complementary surface structures may be toleranced such that the locking guidewire or guide pin may be proximally retracted into the lumen 11 to engage the locking structure, but the locking structure provides a sufficient resistance to distal migration of the locking guide wire 150 such that it is unlikely or impossible to become disengaged under normal use.

Embodiments of an insertion tool 200 for inserting and deploying a bone fixation device are illustrated in FIGS. 10-20. As will be described below, the illustrated insertion tool 200 is particularly configured for deploying bone fixation devices that utilize a pin 26 and a locking guide wire 150 such as the bone fixation devices described above and those described in U.S. Pat. No. 6,632,224 filed Mar. 22, 2001, which is incorporated by reference herein in its entirety. Accordingly, the insertion tool will be described with reference to the locking device described above. However, it should be appreciated, certain features of the insertion tool 200 may also find utility in bone fixation devices that do not utilize a pin and/or a locking guide wire 150.

Figure 10:
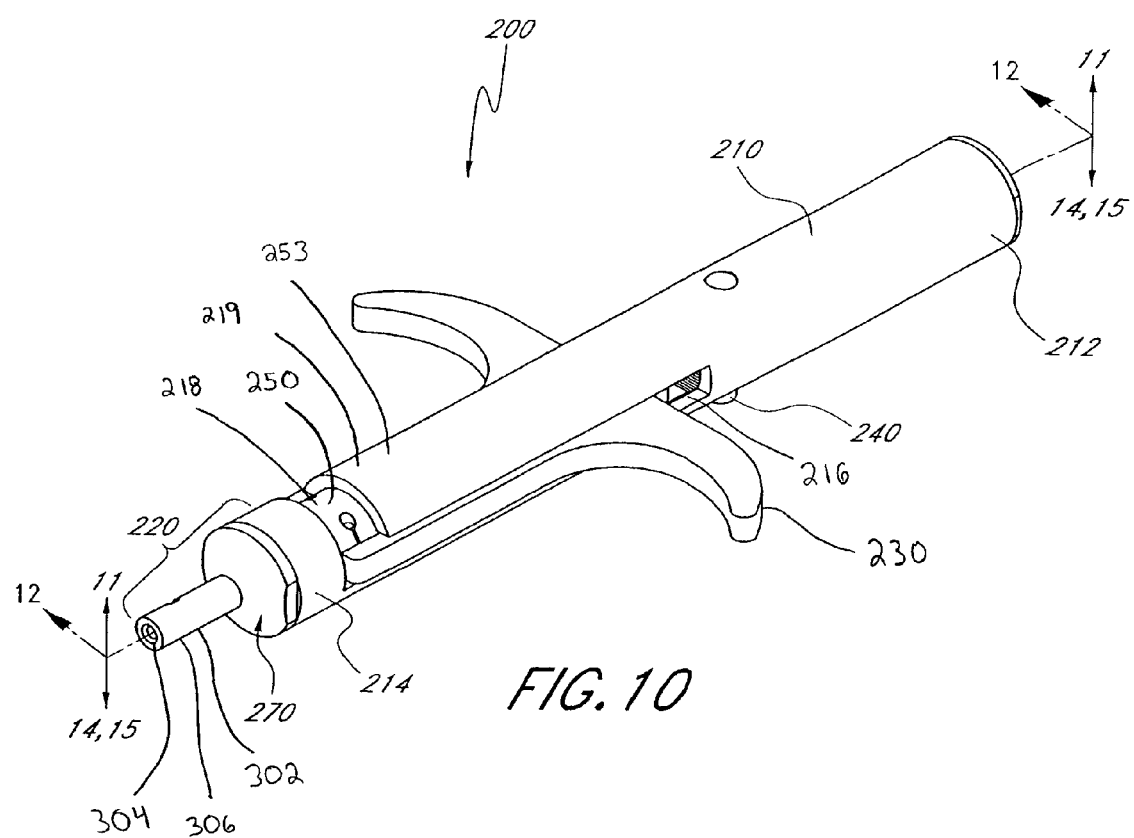
FIG. 10 is a perspective view of a bone fixation device insertion tool having desired features and advantages.

With reference to FIG. 10, the insertion tool 200 of the illustrated embodiment generally comprises an elongate tubular outer body 210, a pair of levers 230, and central member 250 slidably positioned within the tubular outer body 210 and coupled to the levers 230. As will be explained below, the levers 230 are configured to engage the locking guidewire 150. The tool 200 also comprises a distal portion 220 that is coupled to the outer body 210 and is configured to engage the pin 26 of the bone fixation device. The insertion tool 200 is configured to grip and move the locking guidewire 150 in a proximal direction with respect to the pin 26. In this manner, the distal portion 156 of the locking guidewire 150 may be retracted proximally into the first portion 160 (see FIG. 9) of the lumen 11 to resist compression of the lever arms of the pin 26.

Figure 11:
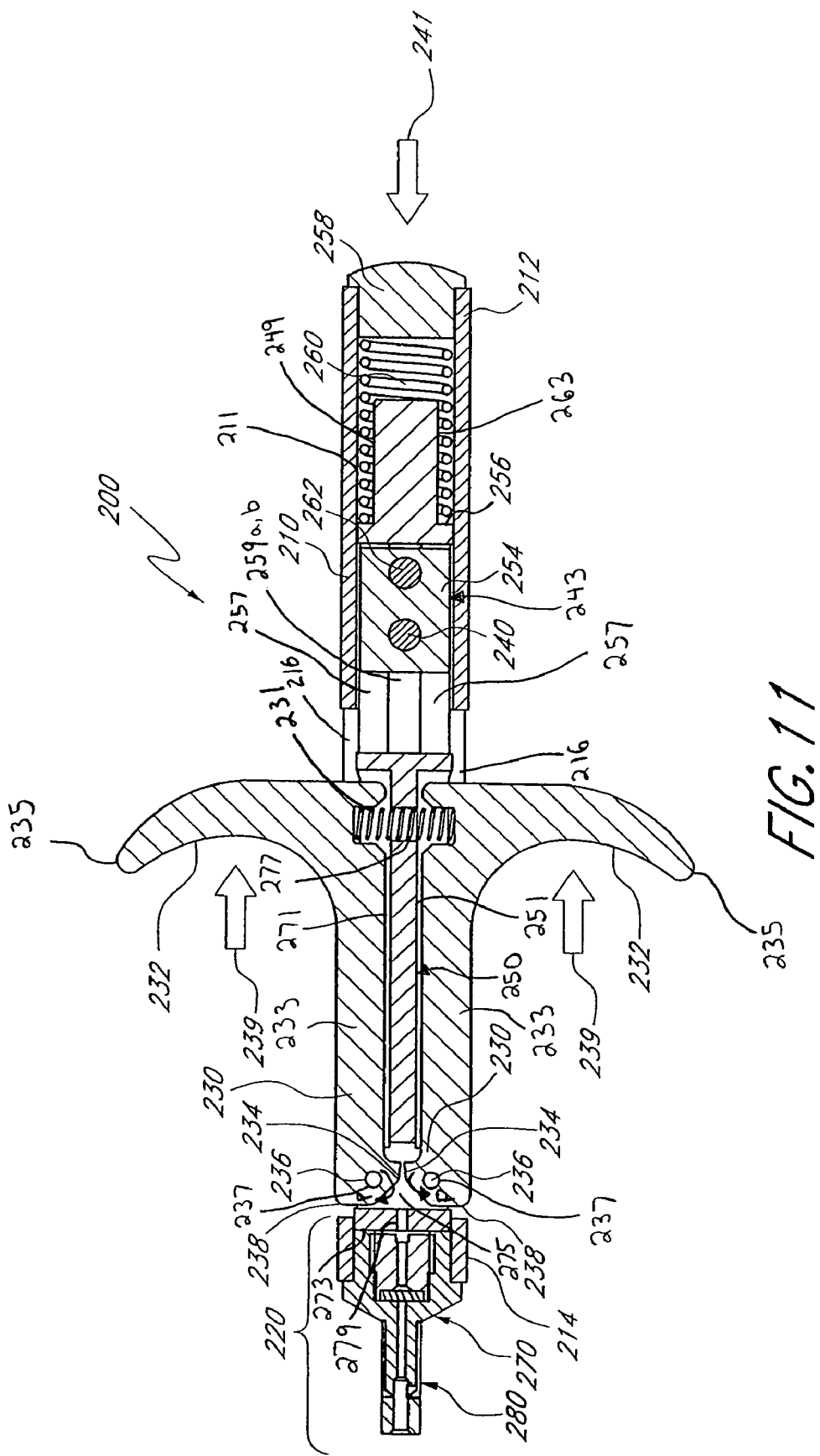
FIG. 11 is a section view of the insertion tool of FIG. 10 taken along line 11-11.

With reference to FIGS. 10 and 11, the outer body 210 is a generally tubular body that has a proximal end 212 and a distal end 214. In the illustrated embodiment, the outer body 210 has a pair of diametrically spaced elongated openings or slots 216 that are configured so that a portion of the levers 230 extend from the outer body 210. The slots 216 may be generally parallel and extend from an opening or window 218, which is between the distal end 214 and an upper body 253 of the outer body 210. In the illustrated embodiment, the levers 230 may slide along the slots 216 in the axial direction and at least a portion of the levers 230 maybe moved away from and/or toward the longitudinal axis of the tool 200. Although not illustrated, the slots 216 and the elongated body 210 may have various shapes and configurations depending on the desired application and deployment environment. In the illustrated embodiment, the outer body 210 is formed from a tubular body having portions removed to form the window 218 and the slots 216. In other embodiments, the outer body 210 may have other cross-sectional shapes (e.g., rectangular, elliptical, etc.)

With reference to FIG. 11, which is a cross-sectional view of the device 200, the outer body 210 has an inner surface 211 that defines a chamber in which the central body 250, a biasing member 260 (e.g., a spring), a ratchet assembly 243, and a portion of the levers 230 are positioned.

The levers 230 preferably comprise finger engagement portions 232, elongated portions or arms 233, and wire gripping portions 234. The levers 230 are configured so that a person can comfortably grip and apply a force on the levers 230. In the illustrated embodiment, the levers 230 of the have generally 'L' or 'J' shape. However, the levers 230 can have any shape or configuration so that a portion of the levers 230 can engage with the bone fixture device (e.g., the locking guidewire 150) when the levers 230 are actuated.

The finger engagement portions 232 are at the proximal ends of the levers 230 and are generally curved, elongated members extending from the arms 233 and out of the outer body 210 (see FIG. 10). The width of the finger engagement portions 232 can be reduced toward the ends 235. The finger engagement portions 232 can be configured to be comfortably engaged by as many fingers of the user as desired. In one embodiment, for example, the finger engagement portions 232 are configured so that a person can use one finger to apply a force to the upper finger engagement portion 232 on one side of the tool 200 and another finger to apply a force to the lower finger engagement portion 232 on the other side of the tool 200 with the body 210 extending between the upper and lower fingers. It should be appreciated that the finger engagement portions 232 can be configured to engage more than one finger of the user.

A further advantage is provided where the ends 235 of the finger engagement portions 232 are curved in the distal direction to prevent a person's finger or fingers from sliding off of the levers 230. Thus, when the person pulls on the levers 230, the finger engagement portions 232 can inhibit outward movement (i.e., away from the longitudinal axis of the tool 200) of the user's fingers. However, those skilled in the art recognize that the finger engagement portions 232 can have other shapes and sizes depending on, for example, the force applied to the levers 230, the size of the user's fingers and hand, the application of the tool 200, and the like.

Figure 16:
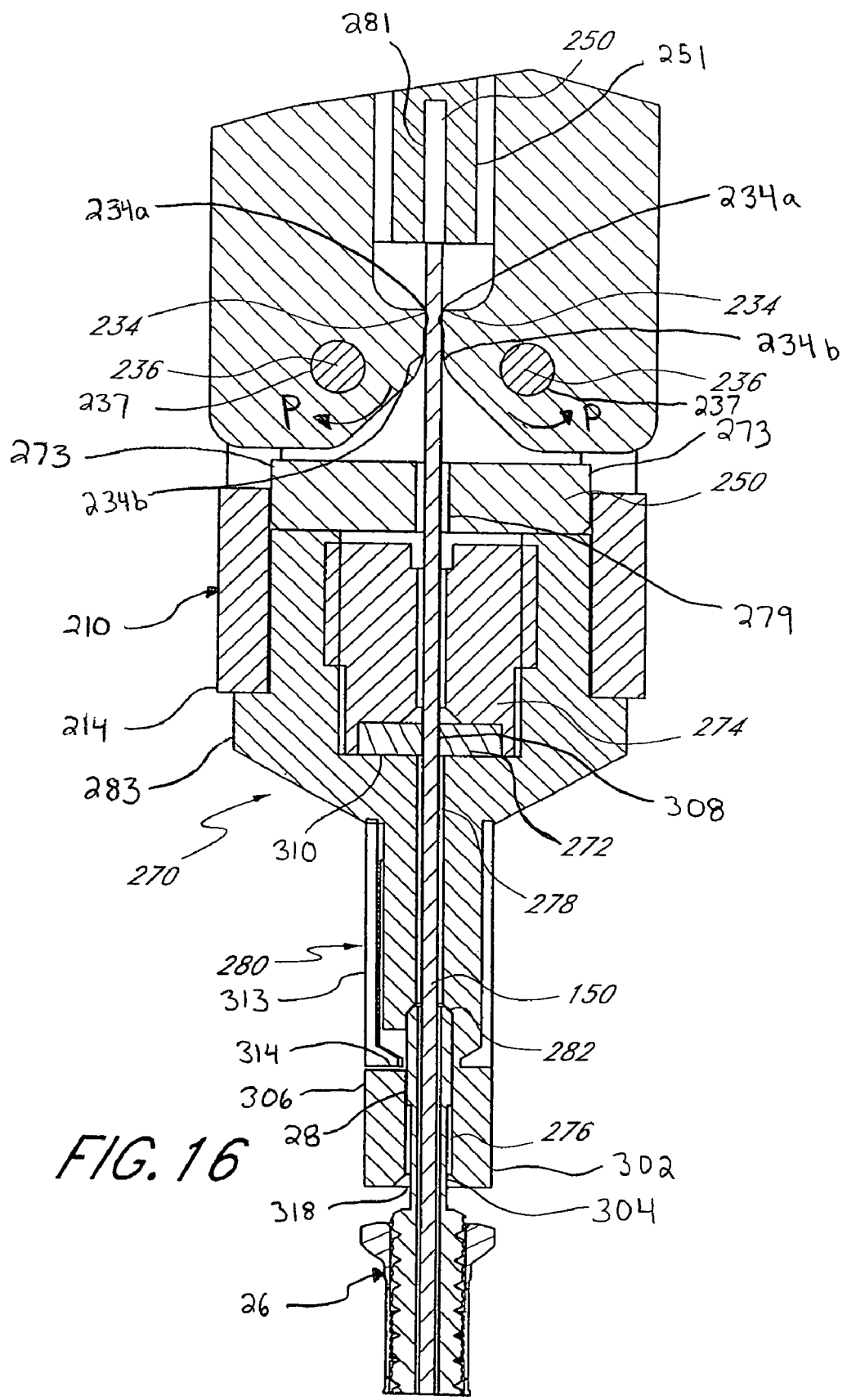
FIG. 16 is a detailed section view of a portion of the insertion tool of FIG. 14 taken along line 16-16.

With continued reference to FIG. 11, the arms 233 of the levers 230 extend from the finger engagement portions 232 to the wire gripping portion 234 near the distal end of the levers 230. A substantial portion of the arms 233 may have a generally rectangular cross-sectional profile. The wire gripping portions 234 are pivotable with respect to the central body 250. Accordingly, in the illustrated embodiment, the wire gripping portions 234 include holes 237 for receiving pivot pins 236. The wire gripping portions 234 can be in the form of tangs or prongs. However, the wire gripping portions 234 can be any shape that can engage and hold a portion of the locking wire 150 when the levers 230 are moved to a certain position. As shown in FIG. 16, the wire gripping portions 234 are configured such that the distance between the proximal portions 234a of the wire gripping portions 234 is less than the distance between distal portions 234b of wire gripping portions 234. Thus, a proximal force 239 (the arrow shown in FIG. 11) causes the proximal portions 235a to pinch the guidewire to inhibit movement of the guidewire. In another embodiment, the distance between the proximal portions 234a and distal portions 234b are generally equal when then levers 230 grip the guidewire. The wire engagement portions 234 may also include features for enhancing the gripping force. For example, in one embodiment, the wire engagement portions 234 have grooves that engage the guidewire of the fixation device to ensure that the guidwire is securely held by the wire engagement portions 234. However, the wire engagement portions 234 can have other surface treatments to achieve the desire interaction between the wire engagement portions 234 and portions of the fixation device. For example, the wire engagement portions 234 can have protuberances, spikes, or textured surface to provide adequate frictional forces between the wire engagement portions 234 and the bone fixture device.

With continued reference to FIG. 11, the holes 237 are located at the distal ends of the levers 230. In one embodiment, the centers of the holes 237 are preferably located distally from at least a portion of the wire gripping portions 234. This arrangement provides mechanical advantage so that the levers 230 securely grip the guide wire 150 when the user applies sufficient force. Thus, the location of the center of the holes 237 with respect to the finger grips 235 can be varied to achieve the desire leverage.

As mentioned above, the levers 230 are mounted to the central body 250 for rotating about the pivot axes defined by the pins 236 along the direction of arrow P to engage the locking wire 150. In the illustrated embodiment, the outer body 210 can be held stationary by, for example, applying a distal force 241 to the outer body while the proximal force indicated by the arrows 239 can be applied to the lever 230 so that the lever pivots about the pivot pin 236 in the direction of the arrow P, thereby causing the proximal end of the lever 230 to move towards the central axis of the tool 200. Thus, the upper lever 230 can be rotated clockwise about its respective pin 236 and the lower lever 230 can be rotated counterclockwise about its respective pin 236. The wire engagement portions 234 of the levers 230 are configured such that as the levers 230 pivot, the wire engagement portions 234 move towards one another, thus allowing a wire or pin positioned therebetween to be gripped.

Figure 14:
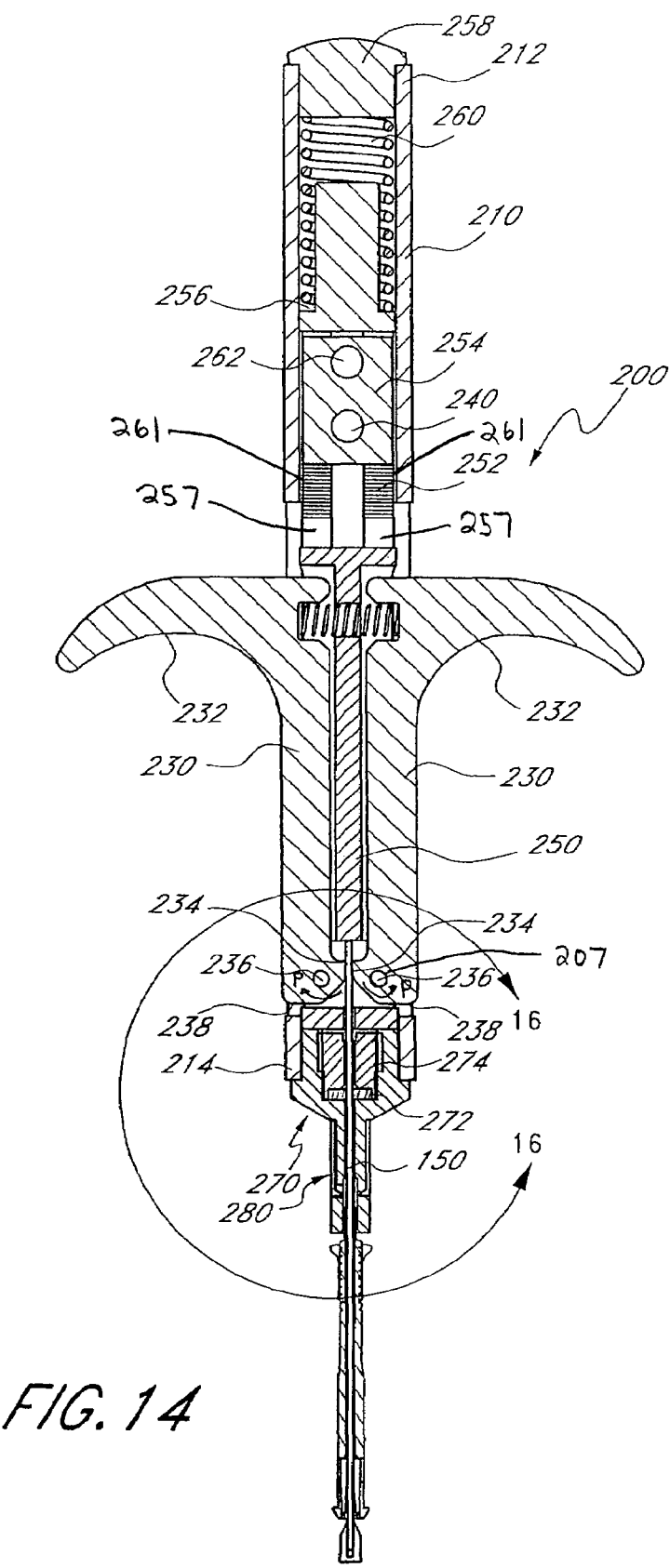
FIG. 14 is a section view of the insertion tool of FIG. 10 taken along line 14-14, shown with a bone fixation device in a first position.
Figure 15:
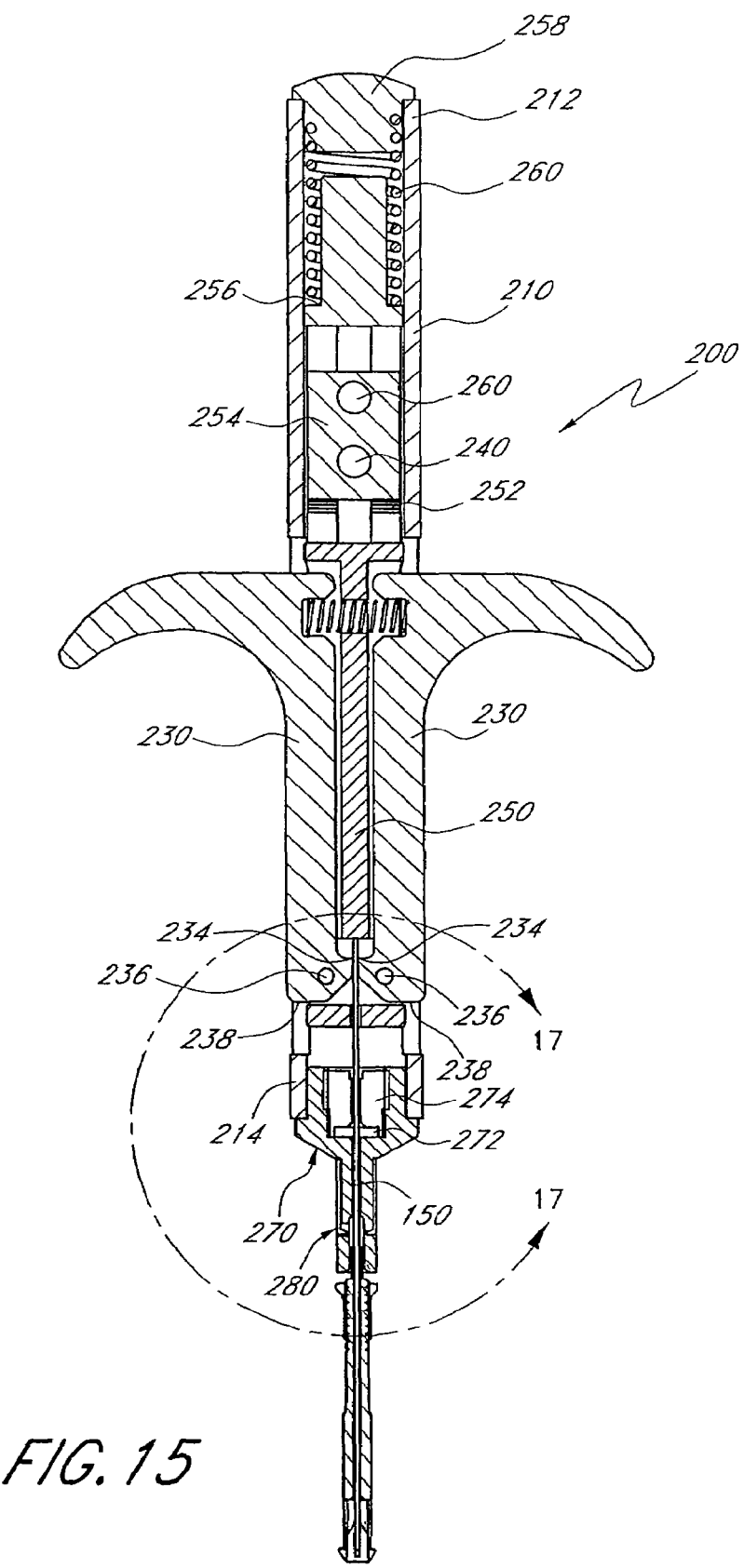
FIG. 15 is a section view of the insertion tool of FIG. 10 taken along line 15-15, shown with a bone fixation device in a second position.

A further advantage of the illustrated embodiment is that the effective length of the lever arms 233 of the levers 230 is chosen to provide a mechanical advantage, thereby allowing a relatively small generally proximal force on the finger engagement portions 232 to tightly grip the locking wire 150 (as shown in FIG. 14) placed between the wire gripping portions 234. Those skilled in the art will understand how to optimize the various dimensions of the levers for the particular needs of a user. Alternatively, however, the tool may be configured to grip a bone fixation device guidewire in response to an axial, angled, rotational and/or otherwise-directed force. Such embodiments may incorporate additional levers, cables, pulleys, or other structures as will be clear to those skilled in the art in view of the present disclosure To disengage the locking wire, the levers 230 may be moved in a distal direction (i.e., opposite the direction of the arrows 239 in FIG. 11) so that the wire-gripping portions 234 disengage the guidewire 150. As shown in FIG. 11, in the illustrated embodiment, the levers 230 may be outwardly biased by a biasing member 231 (e.g., a helical spring) located towards their proximal ends. In this arrangement, the biasing member 231 may extend through an opening or hole 277 formed in the central body 150.

While the preferred embodiment utilizes a pair of lever arms with wire-gripping portions 234 to grip the wire 140, it should be appreciated that in other non-illustrated embodiments other arrangements and devices may be used to grip the wire.

With continued reference to FIG. 11, in the illustrated embodiment, the tool 200 comprises a stop 258 at its proximal end. The stop 258 is coupled to the proximal end 212 of the outer body 210 such that a distal portion of the stop 258 is disposed within the outer body 210 while a distal portion of the stop 258 extends from the outer body 210. The distal portion of the stop 258 can engage the proximal biasing member 260, which can be in the form of a helical spring.

The proximal biasing member 260 is preferably positioned between the stop 258 and a proximal end 249 of the central body 250 to bias the central body 250 in the distal direction. The proximal end 249 has a seat or engagement surface 256 and a cylindrical body 263. In the illustrated embodiment, the proximal end of the proximal biasing member 260 engages the distal end of the stop 258 and the distal end of the proximal biasing member 260 engages the engagement surface 256 of the proximal end 249. A distal portion of the spring 260 surrounds the cylindrical body 263 of the proximal end 249. The cylindrical body 263 advantageously maintains the biasing member 260 in proper position during operation of the tool 200. Preferably the distal portion of the biasing member 260 is between the inner surface 211 of the outer body 210 and the cylindrical body 263.

With reference to FIGS. 11, 11A, 14 and 15, the central body 250 preferably comprises the biasing end 249 (discussed above), a ratchet portion 252, a wall 251, a upper body 253, and a lower body 255. The biasing end 249 is at the proximal end of the central body 250 and the upper and lower bodies 253, 255 are at the other end. The ratchet portion 252 is between the spring end 249 and the bodies 253, 255. The wall 251 is between portions of the upper and lower bodies 253, 255. The central body 250 is preferably slidably disposed within the outer body 210 and more preferably, the central body 250 is concentric with and axially movable within the outer body 210.

As will be explained, the ratchet portion 252 may allow proximal movement of the central body 250 with respect to the outer body 210 while resisting distal movement of the central body with respect to the outer body 210. In the illustrated embodiment, the ratchet portion 252 has a plurality of legs 257 (see e.g., FIGS. 11 and 12) that are coupled to or integrally formed with the biasing end 249 and are configured to allow a portion of the central body 250 to move past a release button 240. In one embodiment, one of the upper and lower legs 257 is on one side of the release button 240 and the other upper and lower legs 257 are on the other side of the release button 240. The plurality of legs 257 form a pair of slots 259. In the illustrated embodiment of FIG. 11A, for example, the pair of upper legs 257 for form the upper slot 259a and the pair of lower legs 257 form the lower slot 259b. The slots 259a, 259b are sized so that the release button 240 is positioned within the slots 259a, 259b such that ratchet portion 252 can move relative to the release button 240.

Figure 12:
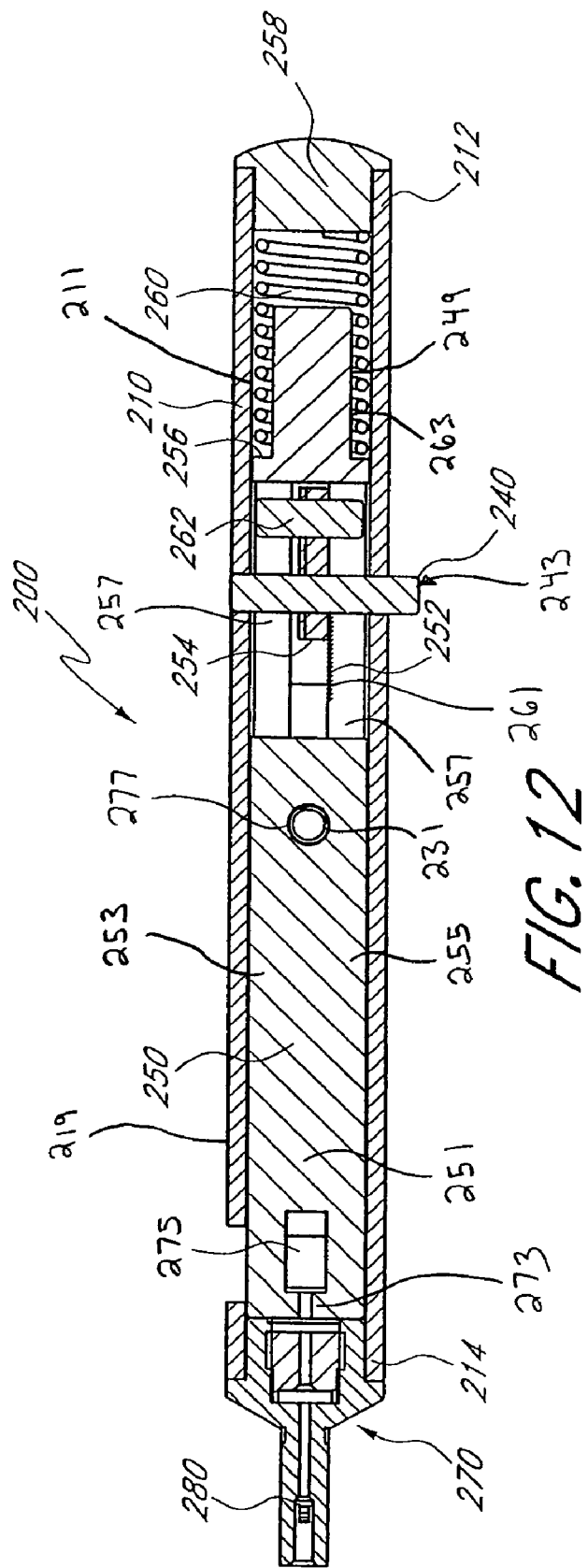
FIG. 12 is a section view of the insertion tool of FIG. 10 taken along line 12-12.
Figure 13:
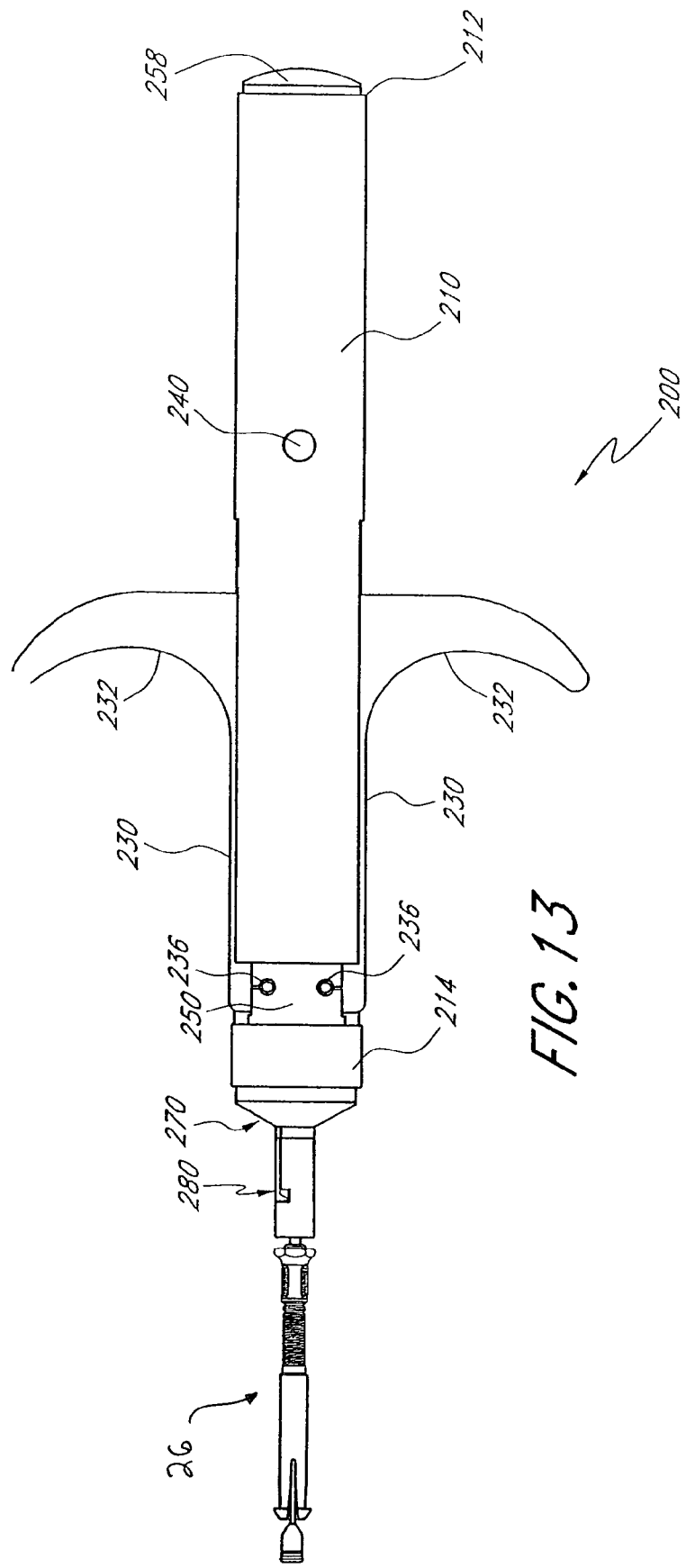
FIG. 13 is an elevation view of the insertion tool of FIG. 10 including a bone fixation device disposed thereon.

With reference to FIGS. 11 and 12, the ratchet portion 252 may comprise any of a variety or retention structures 261 to limit movement of the central body 250 relative the outer body 210. In the illustrated embodiment, the ratchet portion 252 comprises structures 261 in the form of a plurality of ridges or teeth configured to engage a corresponding ratchet plate 254, which is axially immobile relative to the outer body 210. In one embodiment, the lower legs 257 of the ratchet portion 252 have an upper surface forming teeth 261. Preferably, the ratchet plate 254 has corresponding structures, such as teeth, to engage with the teeth 261 of the lower legs 257. However, the structures 261 can be grooves, threads or other suitable structures for cooperating with the ratchet plate 254 to control the movement of the central body 250.

The ratchet plate 254 is configured such that it is biased towards the lower legs 257 of the ratchet portion 252. In this manner, the ratchet plate 254 can be configured to allow unidirectional movement of the central body 250. In the illustrated embodiment, allows the central body 250 to be axially movable in the proximal direction and restrained in a distal direction relative to the outer body 210.

The ratchet plate 254 may be biased using a variety of devices and methods recognized by those skilled in the art. For example, in the illustrated embodiment, a biasing pin 262 (see e.g., FIG. 12) biases the ratchet plate 254 towards the lower leg 257 and can be sized and disposed-such that it will engage opposite walls of the outer body 210, and thus resist rotation about its transverse axis. The biasing pin 262 is disposed in a hole in the ratchet plate 254 (see FIG. 11) such that the ratchet plate 254 will also resist rotation about the transverse axis of the biasing pin 262. Thus, the biasing pin 262 can ensure that the lower surface of the ratchet plate 254 engages the upper surface of the lower legs 257. In other embodiments, other suitable devices and structures that can be used to bias the ratchet plate 254. For example, a spring can be used in combination with the biasing pin 262 to ensure that the ratchet plate 254 provides the desired travel of the central body 250.

The release button 240 (see FIGS. 11 and 12) is preferably provided to allow the ratchet plate 254 to release the central body 250. After the central body 250 is released, the central body 250 may be returned to its original distal position by the bias of the biasing member 260. In the illustrated embodiment, the release button 240 is a generally cylindrical member that extends from opposite walls of the outer body 210 and is coupled to the ratchet plate 254. Preferably, the outer body 210 has a pair of diametrically spaced holes or openings for receiving the release button 240. The release button 240 is therefore axially immobile relative the outer body 210 therefore resulting in the ratchet plate 254 also being axially immobile relative the outer body 210.

In the illustrated embodiment of FIG. 12, the release button 240 is in a first position so that the ratchet plate 254 engages with the legs 257 and inhibits movement of the central body 250 in the distal direction. When the release button 240 is in the first position, the lower portion of the release button 240 extends from the outer body 210. The release button 240 can be moved vertically to a second position (not shown) so that the upper portion of the release button 240 extends from the outer body 210. The user can move the release button 240 to the second position by applying a force in the vertical direction to the release button 240. When the release button 240 is in the second position, the ratchet plate 254, which is coupled to the release button 240, is spaced from the lower legs 257 such that the teeth of the ratchet plate 254 disengages the teeth 261 of the lower legs 257. The central body 250 can slide in either the distal or proximal direction when the release button 240 is in the second position. Although not illustrated, those of skill in the art will recognized other suitable arrangements and positions for the release button 240.

The biasing pin 262 and release button 240 may be coupled to the ratchet plate 254 by a press fit, welds, adhesives, threads, or other mechanical fastener, or any other method recognized by those skilled in the art. In the illustrated arrangement, the release button 240 and biasing pin 262 are preferably sized to be press fitted tightly within the respective holes in the ratchet plate 254. Alternatively, the release button 240 and/or biasing pin 262 may comprise annular ridges or grooves configured to interact with corresponding structures on the ratchet plate 254 such that the release button 240 and the biasing pin 262 are substantially fixed relative to the ratchet plate 254.

As mentioned above, the ratchet portion 252 may allow proximal movement of the central body 250 with respect to the outer body 210 while resisting distal movement of the central body with respect to the outer body 210. The release button 240, in turn, disengages the ratchet portion 252 such that distal movement of the central body 250 is permitted. While the above described structure represents a preferred embodiment, it should be appreciated that other devices and structures may be provided for selectively allowing proximal movement of the central body 250 with respect to the outer body 210 while resisting distal movement of the central body with respect to the outer body 210.

Figure 11A:
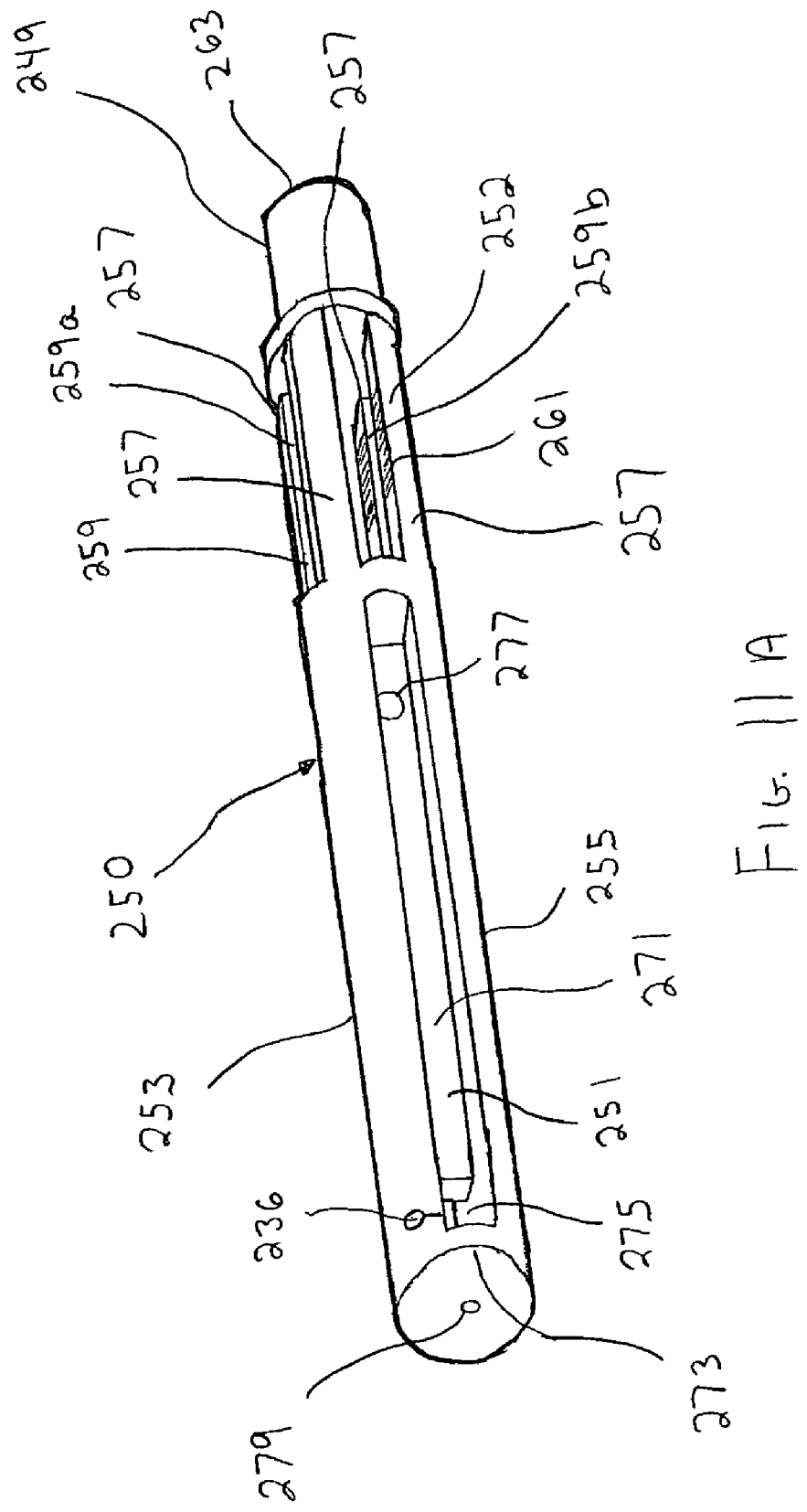
FIG. 11A is a side perspective view of a central portion of the insertion tool of FIG. 10.

With reference now to FIG. 11A, the wall 251, upper body 253 and lower body 255 of the central body 250 can be coupled or integrally formed with the distal end of the ratchet portion 252. The wall 251 and bodies 253, 255 cooperate to define a window 275 and slots or channels 271 that can receive at least a portion of the levers 230.

In the illustrated embodiment, the wall 251 is connected the upper body 253 and the lower body 255 and defines the bottom of the channels 271. The wall 251 extends from a location near the ratchet portion 252 to the proximal side of the window 275. The proximal portion of the wall 251 has the opening or hole 277 for receiving at least a portion of the biasing member 231 as discussed above. In the illustrated embodiment, the opening 277 is generally circular and is sized to surround the central portion of the biasing member 231, as shown in FIG. 11. Those skilled in the art recognize that opening 277 can be at various positions depending on the configuration of the levers 230.

With reference to FIG. 11, in the illustrated embodiment, the wall 251 has a generally uniform width and is disposed between a portion of the pair of levers 230. However, the wall 251 can have other suitable shapes depending on, for example, the size of the opening 277 and the desired movement of the levers 230. As shown in FIG. 16, for example, the wall 251 can comprise at least a partial axial opening or hole 281 for receiving the guide wire 150. The proximal end of the guide wire 150 can be inserted and advanced along the hole 281.

With reference back to FIG. 11A, in the illustrated embodiment, the upper body 253 is connected to the upper portion of the wall 251 and defines the upper side of the channel 271. The upper body 253 has a generally semi-circular cross-section along its length. The upper surface of the upper body 253 is curved to mate with the inner surface 211 of the outer body 210 (see e.g., FIG. 12). The upper surface of the central body 250 can slidably engage the inner surface 211 of the outer body 210 so that the central body 250 can easily slide within the outer body 210. The lower body 255 is connected to the lower portion of the wall 251 and defines the lower side of the channel 271. The lower body 255 also has a generally semi-circular cross-section along its length. The lower surface of the upper body 255 is curved to mate with the inner surface 211 of the outer body 210. The lower surface of the lower body 255 can slidably engage the inner surface 211 of the outer body 210 so that the central body 250 can easily slide within the outer body 210. Although not illustrated, in other embodiments, the lower and upper bodies 253, 255 can have other suitable shapes depending on the desired size and configuration of the channel 271 and/or the outer body 210.

A distal wall 273 (see FIG. 11A) extends from the upper body 253 to the lower body 255. The distal wall 273 has a opening or hole 279 for receiving the locking wire 150 as shown in FIG. 16. The hole 279 can prevent substantial lateral movement of the guidewire and can ensure that the guidewire is located in the desired position. The hole 279 can position the guide wire 150 equidistant between the pivot pins 236. Thus, when the user applies proximal forces to the levers 230, the wire engagement portions 234 can contact the guide wire 150 at approximately the same time and maintain the desired position of the guide wire 150. For example, the guide wire 150 can remain substantially straight during use of the tool 200, thus preventing bending of the guide wire 150.

With reference to FIGS. 11 and 11A, the channels 271 receive at least a portion of the levers 230 and the biasing member 231. The channels 271 in this arrangement facilitate proper movement of the levers 230 about their respective pivot pins 236. The walls or sides of the channels 271 also preferably limit the vertical movement of the levers 230.

With reference to FIGS. 11, 11A and 12, a window 275 is formed between the wall 251 and the distal wall 273. The window 275 is configured to receive at least a portion of the wire engagement portions 234 of the levers. As shown in FIG. 14, the guide wire 150 can pass through the window 275.

Figure 17:
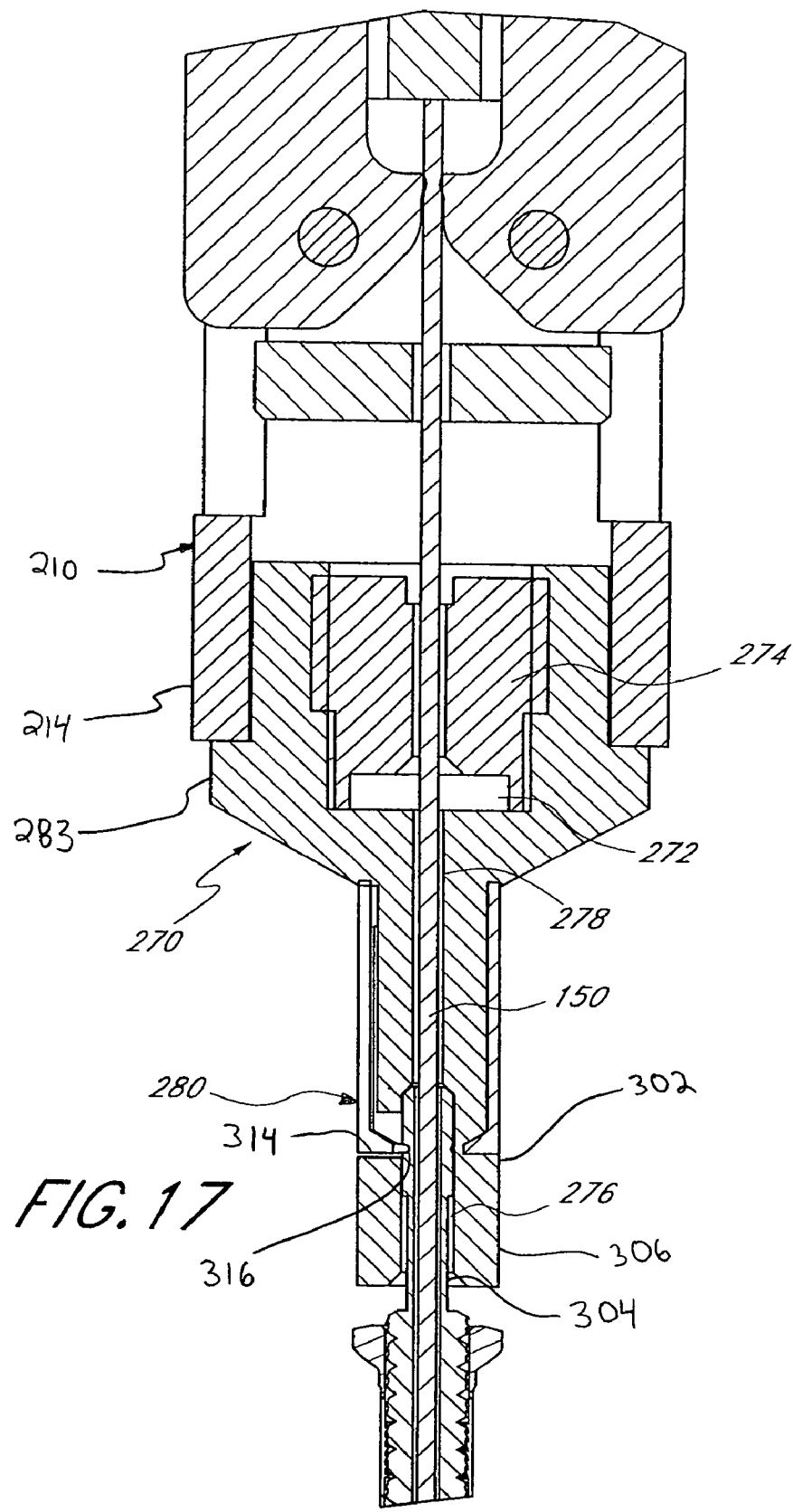
FIG. 17 is detailed section view of a portion of the insertion tool of FIG. 15 taken through line 17-17.

As shown in FIGS. 11 and 12, the distal portion 220 of the tool 200 is preferably configured for receiving and at least temporarily retaining a proximal pin 26 of the bone fixation device. With particular reference to. FIGS. 16 and 17, the distal portion comprises a distal cap 270 that is attached to the distal end 214 of the outer body 210. The distal cap 270 comprises a housing 283, a washer 272, a washer positioning screw 274, and a pin-gripping lever arm 280. The distal cap 270 also defines a wire receiving lumen 278 for receiving a portion of a bone fixation device. In the illustrated embodiment, for example, the wire receiving lumen 278 can receive the guide wire 150.

The housing 283 comprises a tip 302 for receiving a portion of a bone fixation device (e.g., the pin 26). The tip 302 comprises an opening 304 and a body 306 that defines at least a portion of a pin receiving lumen 276. As shown in FIGS. 16 and 17, the opening 304 is sized so that the proximal end 28 of the pin 26 may be passed through the opening 304 and along the pin receiving lumen 276. The proximal portion of the tip 302 is preferably adapted to receive the pin-gripping arm 280. In the illustrated embodiment, the outer surface of the pin-gripping arm 280 is generally flush with the outer surface of the tip 302.

The housing 283 can be coupled to the distal end 214 of the outer body 210 and can extend from the distal wall 273 of the central body 250 and past the pin-gripping arm 280. In the illustrated embodiment, the proximal portion of the housing 283 is disposed within the distal opening of the outer body 210. The housing 283 defines cylindrical chamber that surrounds the washer 272, the washer positioning screw 274, and a portion of the wire 150.

With reference to FIG. 16, the washer 272 advantageously inhibits fluid from passing through the tool 200. In the illustrated embodiment, the washer 272 forms a seal 308 with the guide wire 150, which is inserted through the washer, so that fluid (e.g., blood) is prevented from migrating between the wire 150 and the washer 272 and into the gripping mechanism of the insertion tool 200. The washer 272 may also provide a friction or elastic fit between the washer 272 and the guide wire 150 so as to hold the guide wire 150 in place. The washer 272 may also form a seal 310 between the washer 272 and the inner surface of the housing 283. Preferably the seals 308, 310 prevent fluid from passing proximal the washer 272. The washer 272 is typically made of a flexible material such as rubber, latex, or other pliable material. The washer 272 can also be constructed from other types of materials with suitable sealing characteristics. One of ordinary skill in the art can determine the appropriate combination of material type, thickness, and shape to achieve the desired seals for preventing fluid flow into the mechanisms of the tool 200.

In the illustrated embodiment, the washer positioning screw 274 holds and positions the washer 272 in the housing 283. The washer positioning screw 274 of this arrangement has a generally cylindrical body having a proximal portion that engages the proximal portion of the inner surface of the housing 283. The distal end of the washer positioning screw 274 has a circular recess for receiving the washer 272. A portion of wire-receiving lumen 278 is defined by the by the washer positioning screw 274 so that the guide wire 150 can pass through the washer positioning screw 274. In one embodiment, the washer positioning screw 274 has threads on a portion of its proximal end and the housing has corresponding threads, such the washer positioning screw 274 and the housing 283 can be thread ably coupled. The desired seal 310 between the washer 272 and the housing 283 can be achieved by rotating the screw 274 relative the housing 283 to cause relative axial movement between the screw 274 and the housing 283. For example, if fluid migrates through the seal 310, the screw 274 can be rotated relative the housing 283 so that the screw moves in the distal direction thereby pushing the washer 272 against the housing 283. In this manner, the washer 272 can be compressed between the screw 274 and the housing 283 until the desired seal 310 is achieved. In another embodiment, the screw 274 is provided without threads and is sized to fit substantially tightly within the housing 283. Although not illustrated, other types of members can be preferably tightly fit into the distal cap 270 to ensure that proper seals are formed by the washer 272.

The screw 274 can be made of a material such as rubber, plastic, metal, and pliable materials. The screw 274 can also be constructed from other types of materials with suitable sealing characteristics. One of ordinary skill in the art can determine the appropriate combination of material type, thickness, and shape to achieve the desired seals for preventing fluid flow into the mechanisms of the tool 200.

With continued reference to FIG. 16, the pin-gripping arm 280 may comprise a variety of structures configured to preferably removably hold a bone fixation device (e.g., the pin 26) within the pin-receiving lumen 276. In the illustrated embodiment, the pin-gripping arm 280 comprises a lever arm 313 with a pin-engaging ridge or tang 314. The end of tang 314 can be configured and sized to hold the pin 26. In the illustrated embodiment of FIG. 17, the pin of the bone fixation device may be provided with an annular ridge or groove 316 sized and positioned to receive the end of the tang 314 of the pin-gripping arm 280 such that the bone fixation pin is preferably held substantially rigidly by the insertion tool 200. Thus, the pin-gripping arm 280 inhibits substantial axial movement of the pin 26 relative to the tool 200. The tang 314 can be outwardly moved to disengage the pin-gripping arm 280 so that the pin 26 can be removed from the tool 200. The tang 314 of the pin-gripping arm 280 and the groove 316 of the pin 26 can have various suitable shapes and sizes to achieve the desired pin 26 attachment. For example, the groove 316 can have a generally U-shaped profile and the end of the tang 314 can have a similar shape. In some embodiments, the groove 316 has a generally V-shaped profile and the end of the tang 314 can have a similar shape.

With continued reference to FIG. 16, the pin-receiving lumen 276 typically includes a pin stop 282 to allow a sufficient length of the pin to be inserted into the lumen 276. The distal end of the pin-receiving lumen 276 forms the opening 304. The tang 314 is disposed midway between the proximal and distal end of the pin-receiving lumen 276. In the illustrated embodiment, the diameter of the pin-receiving lumen 276 is reduced at its distal end. That is, the tip 302 can have an annular ridge 318 at its distal end where the inner surface of the ridge 318 defines the opening 304.

Figure 18:
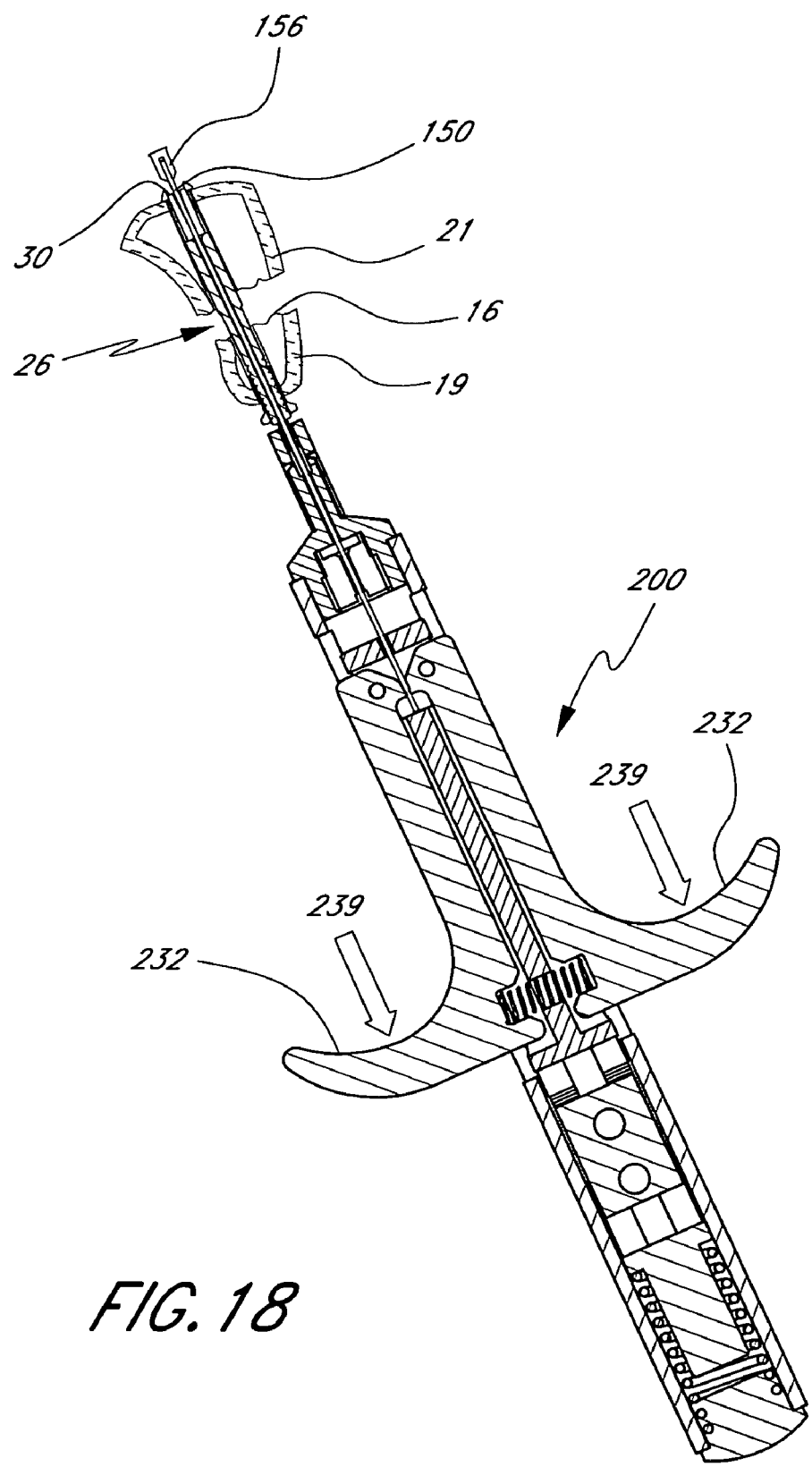
FIG. 18 is a sectional schematic illustration of a bone fixation device and an insertion tool, the bone fixation device being inserted across a fractured bone.
Figure 19:
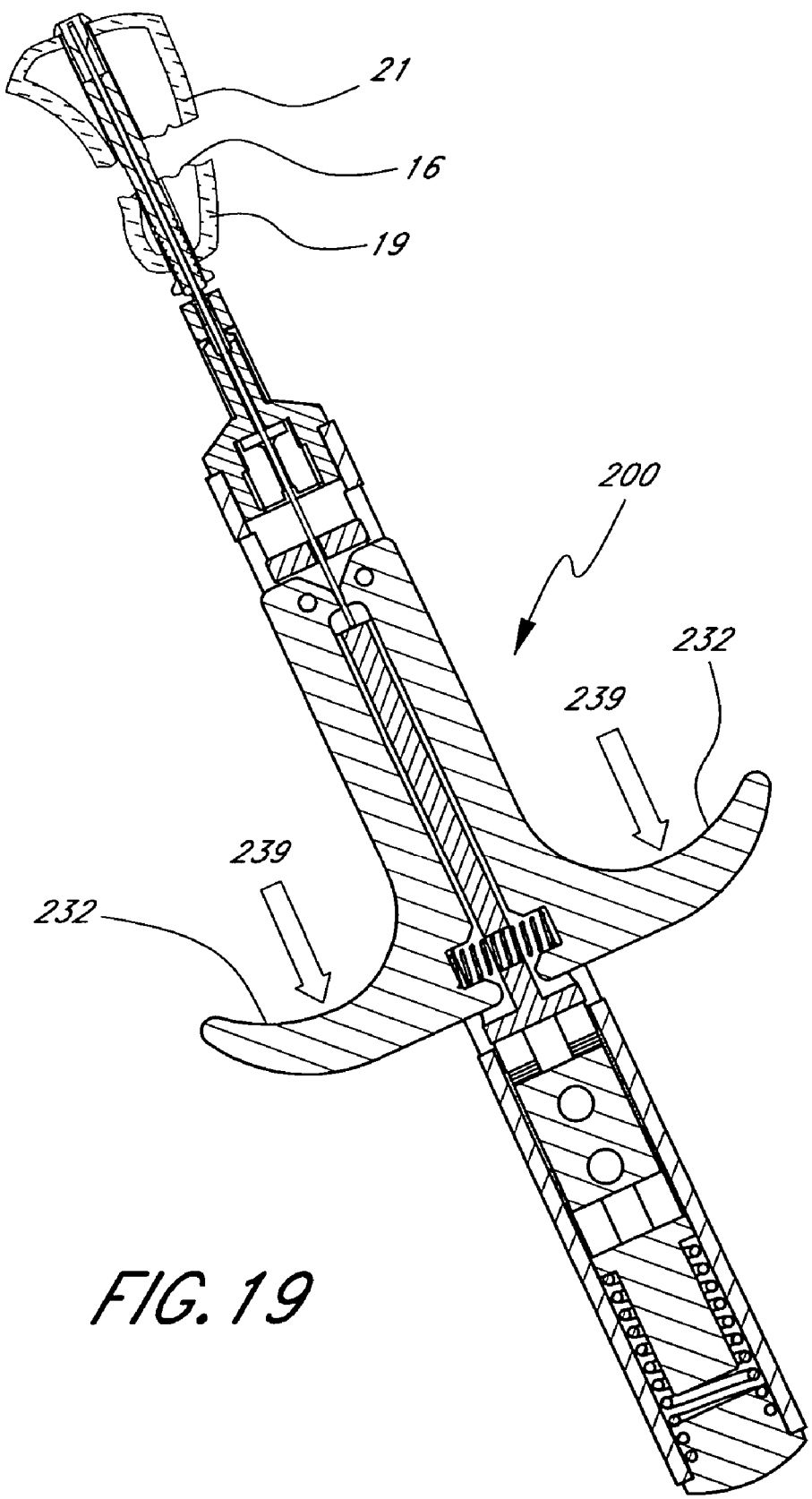
FIG. 19 is a sectional schematic illustration of a bone fixation device and an insertion tool, the bone fixation device being anchored across a fractured bone.
Figure 20:
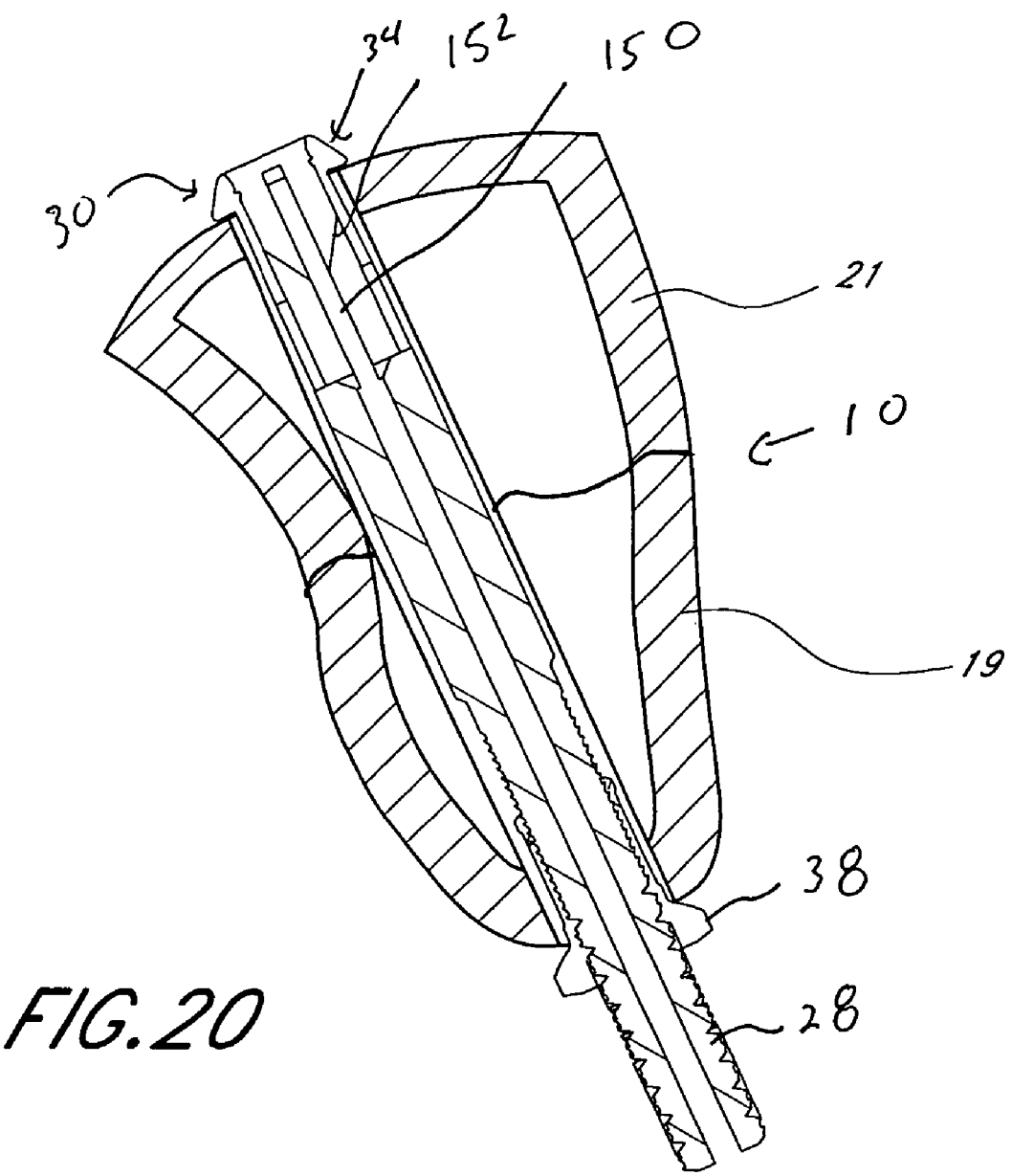
FIG. 20 is a sectional schematic illustration of a bone fixation device being used to secure first and second fragments of a fractured bone.

The operation of a bone fixation device 25 and insertion tool 200 according to one embodiment of use will now be described with reference to FIGS. 18-20. After the clinician accesses the bone, a bone drill is selected and the clinician drills a hole 290 (or 22 in FIG. 1) through the two pieces of bone. A bone fixation device 25 may be inserted into the insertion tool 200 directly from a package, thereby preferably maintaining the sterility of the fixation device 25. In the illustrated embodiment, with reference to FIGS. 16 and 17, the bone fixation device 25 is inserted into the insertion too by inserting the proximal end of the guide wire 150 into the opening 304 and advanced along the wire receiving lumen 278 until the desired portion of the guide wire 150 is between the wire gripping portions 234 of the levers 230. The proximal end 28 of the pin 26, in turn, is inserted into the opening 304 and advanced along the pin receiving lumen 276 until it contacts or is near the pin stop 282. In a modified embodiment, the guidewire 150 and pin 26 may be pre-positioned in the insertion tool 200 and packaged together in a sterile package.

Using the insertion tool to hold the device 25, the distal portion 156 of the guide wire 150 and the distal end 30 of the pin 26 are advanced into the passage 290 until the barbs 50 exit the passage 290. In a non-through bore application (not illustrated), the pin 26 is advanced until the barbs are advanced a sufficient distance into the bone as determined by the clinician. In other embodiments, a different tool or the clinician's hand may be used to insert the fixation device 25 into the passage 290.

With the guide wire 150 positioned within the insertion tool 200, the clinician may apply a proximal force on the finger engagement portions 232 of the insertion tool while holding the outer body 210 relatively stationary. Preferably, the biasing member 260 provides a sufficient distal force on the biasing end 249 of the central body 250 so that the levers 230 rotate about the pivot pins 236 and can securely grip the guide wire 150 while the central body 250 is generally stationary relative the outer body 210 of the tool 200. After the levers 230 grip the guidewire 150, the user can provide sufficient proximal force to overcome the bias of the spring 260 and move the levers 230, which are gripping the guide wire 150, thereby moving the central body 250 in the proximal direction relative the outer body 210 of the tool 200. In the illustrated embodiment, the levers 230 and the central body 250 can be moved in the proximal direction until the proximal end of the biasing end 249 of the central body 250 contacts the distal end of the biasing stop 258. Alternatively, the proximal movement of the levers 230 and central body 250 relative the outer body 210 can be stopped when the bias of the spring 260 overcomes the proximal force applied by the clinician.

As the levers 230 and central body 250 slide within and along the outer body 210, the levers 230 grip and pull the guidewire 250 while the tip 302 holds the pin 26 stationary relative the outer body 210. Thus, the application of a proximal force on the finger engagement portions 232 will preferably result in retraction of the guide wire 150 relative to the pin 26. The guide wire 150 is preferably retracted until the distal portion 156 enters, at least partially, the first portion 160 of the pin 26 (see FIG. 9). As such, at least a part of the distal portion 156 of the guide wire 150 becomes locked within the first portion 160 of the pin 26. This prevents the barbs 50 and lever arms 24 from being compressed radially inward and ensures that the barbs 50 remain seated snugly against the distal component 21 of the bone. Preferably, the outer surfaces of the barbs 50 contact inner surface of the passage 290 to provide frictional forces that inhibit movement of the pin 26 along the passage 290. As mentioned above, in certain embodiments, the distal portion 156 may expand the lever arms 24 beyond their natural relaxed diameter.

The insertion tool 200 can be configured such that the maximum distance which the central body 250 is allowed to move (and thus the maximum distance a wire may be pulled) corresponds to a maximum distance necessary for properly deploying the distal portion 156 of the guide wire 150 within the first portion 160 of the pin 26. Alternatively, additional structures may be provided in order to indicate a degree of retraction of the guide wire 150. For example, a viewing window may be provided to allow a clinician to visually verify the grip and the distance of retraction of a guidewire.

Once the distal portion 156 of the guide wire 150 has been set within the first portion of the pin, the proximal anchor 36 may be rotated or otherwise distally advanced (e.g., by proximally retracting the pin) with respect to the pin body 26 so as to seat the proximal anchor 36 snugly against the proximal component 19 of the bone 10. Proximal retraction or distal advancement of the fixation device may require additional tools. For example, the deployment device described in co-pending application entitled "DEPLOYMENT TOOL FOR DISTAL BONE ANCHORS WITH SECONDARY COMPRESSION", Attorney Docket No. TRIAGE.019A, filed Mar. 1, 2004 and which is incorporated by reference as part of the specification of this application, or similar devices may be used to distally advance the proximal anchor 36 and/or proximally retract the pin body 26 with respect to the proximal anchor 36. Alternatively, features of such tools may be combined with the insertion tool described herein to produce proximal retraction or distal advancement. It should be appreciated that the proximal anchor 36 may be positioned on the bone fixation device 25 prior to positioning of the pin body 32 in the hole or passage 290 or 22, or following placement of the pin body 32 within the through passage 290 or 22.

Following appropriate tensioning of the proximal anchor 36, the proximal end 28 of the pin body 32 and the proximal end 154 of the guide wire 150 are preferably cut off or otherwise removed. These components may be cut using conventional bone forceps which are routinely available in the clinical setting, or snapped off using designed break points as has been discussed.

The tool 200 is preferably adapted to be removably coupled to the bone fixation devices so that the tool 200 can rapidly and conveniently deliver and deploy the fixation device. The tool 200 may also be reused in a similar manners to deliver a plurality of bone fixation devices. Thus, a single tool 200 can deliver a plurality of bone fixture devices during a surgical operation. In practice, various embodiments described above can be provided in a kit. The kit preferably comprises the tool 200 and at least one bone fixation device. In one embodiment, the kit comprises a plurality of bone fixation devices that be rapidly delivered by using the tool 200. The plurality of bone fixation devices can comprise the pin 26, the guidewire 150, and other components described herein.

The method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although certain preferred embodiments and examples have been described herein, it will be understood by those skilled in the art that the present inventive subject matter extends beyond the specifically disclosed embodiments to other alternative embodiments and/or uses of the invention and obvious modifications and equivalents thereof. Thus, it is intended that the scope of the present inventive subject matter herein disclosed should not be limited by the particular disclosed embodiments described above, but should be determined only by a fair reading of the claims that follow.

What is claimed is:

1. A method of fixing a first piece of bone to a second piece of bone comprising the steps of:
providing a pin having at least one laterally moveable distal anchor and a lumen extending therethrough;
advancing the distal anchor through the first piece of bone and into the second piece of bone while the distal anchor is permitted to move laterally inwardly as needed;
gripping with a deployment tool a proximal portion of a wire that extends axially through the lumen; and
proximally retracting with the deployment tool the wire axially through the lumen such that a distal portion of the wire resists radial inward deflection of the distal anchor, thereby locking the distal anchor with respect to lateral inward movement;
wherein the step of proximally retracting with the deployment tool the wire axially through the lumen comprises moving an outer body of the deployment tool with respect to a central body of the deployment, tool; and
wherein the step of moving the outer body of the deployment tool with respect to the central body of the deployment tool comprises one way ratchet-type motion.

2. A method of fixing a first piece of bone to a second piece of bone as in claim 1, wherein the step of gripping with a deployment tool a proximal portion of a wire comprises moving ends of a pair of lever arms toward each other.

3. A method of fixing a first piece of bone to a second piece of bone as in claim 2, wherein the step of moving the ends of a pair of lever arms towards each other comprises applying a proximal force to an opposite end of the pair of lever arms.

4. A method of fixing a first piece of bone to a second piece of bone as in claim 3, wherein the proximal force is, applied by the fingers of a hand holding the deployment tool.

5. A method of fixing a first piece of bone to a second piece of bone as in claim 4, wherein the outer and central bodies of the deployment tool extend between at least the fingers applying the proximal force.

6. A method of fixing a first piece of bone to a second piece of bone as in claim 5, wherein the palm of the hand holding the deployment device prevents proximal movement of the central body with respect to the outer body.

7. A method of fixing a first piece of bone to a second piece of bone comprising the steps of:
providing a pin having at least one laterally moveable distal anchor and a lumen extending therethrough;
advancing the distal anchor through the first piece of bone and into the second piece of bone while the distal anchor is permitted to move laterally inwardly as needed;
gripping with a deployment tool a proximal portion of a wire that extends axially through the lumen; and
moving with the deployment tool the wire axially through the lumen such that a distal portion of the wire resists radial inward deflection of the distal anchor, thereby locking the distal anchor with respect to lateral inward movement;
wherein the step of moving with the deployment tool the wire axially through the lumen comprises moving an outer body of the deployment tool with respect to a central body of the deployment, tool; and wherein the step of gripping with a deployment tool a proximal portion of a wire comprises moving ends of a pair of lever arms toward each other.

8. A method of fixing a first piece of bone to a second piece of bone as in claim 7, wherein the step of moving the ends of a pair of lever arms towards each other comprises applying a proximal force to an opposite end of the pair of lever arms.

9. A method of fixing a first piece of bone to a second piece of bone as in claim 8, wherein the proximal force is, applied by the fingers of a hand holding the deployment tool.

10. A method of fixing a first piece of bone to a second piece of bone as in claim 9, wherein the outer and central bodies of the deployment tool extend between at least the fingers applying the proximal force.

11. A method of fixing a first piece of bone to a second piece of bone as in claim 10, wherein the palm of the hand holding the deployment device prevents proximal movement of the central body with respect to the outer body.

12. A method of fixing a first piece of bone to a second piece of bone comprising the steps of:

providing a pin having at least one laterally moveable distal anchor and a lumen extending therethrough;

advancing the distal anchor through the first piece of bone and into the second piece of bone while the distal anchor is permitted to move laterally inwardly as needed;

gripping with a deployment tool a proximal portion of a wire that extends axially through the lumen; and moving with the deployment tool the wire axially through the lumen such that a distal portion of the wire resists radial inward deflection of the distal anchor, thereby locking the distal anchor with respect to lateral inward movement;

wherein the step of gripping with a deployment tool a proximal portion of a wire comprises moving ends of a pair of lever arms toward each other.

13. A method of fixing a first piece of bone to a second piece of bone as in claim 12, wherein the step of moving the ends of a pair of lever arms towards each other comprises applying a proximal force to an opposite end of the pair of lever arms.

14. A method of fixing a first piece of bone to a second piece of bone as in claim 13, wherein the proximal force is, applied by the fingers of a hand holding the deployment tool.

15. A method of fixing a first piece of bone to a second piece of bone as in claim 14, wherein the outer and central bodies of the deployment tool extend between at least the fingers applying the proximal force.

16. A method of fixing a first piece of bone to a second piece of bone as in claim 15, wherein the palm of the hand holding the deployment device prevents proximal movement of the central body with respect to the outer body.

17. A method of fixing a first piece of bone to a second piece of bone comprising the steps of:

providing a pin having at least one laterally moveable distal anchor and a lumen extending therethrough;

advancing the distal anchor through the first piece of bone and into the second piece of bone while the distal anchor is permitted to move laterally inwardly as needed;

gripping a proximal portion of a wire that extends axially through the lumen; and proximally retracting the wire axially through the lumen using a deployment tool such that a distal portion of the wire resists radial inward deflection of the distal anchor, wherein proximally retracting the wire includes moving an outer body of the deployment tool with respect to a central body of the deployment tool, thereby locking the distal anchor with respect to lateral inward movement.

18. A method of fixing a first piece of bone to a second piece of bone as in claim 17, wherein the step of gripping a proximal portion of a wire includes gripping the proximal portion of the wire with a deployment tool.

19. A method of fixing a first piece of bone to a second piece of bone as in claim 17, wherein moving the outer body of the deployment tool with respect to the central body of the deployment tool comprises one way ratchet-type motion.

\* \* \* \* \*

UNITED STATES PATENT AND TRADEMARK OFFICE
CERTIFICATE OF CORRECTION

| | | |
|---|---|---|
| PATENT NO. | : 7,686,807 B2 | Page 1 of 1 |
| APPLICATION NO. | : 10/790670 | |
| DATED | : March 30, 2010 | |
| INVENTOR(S) | : Martin Padget et al. | |

It is certified that error appears in the above-identified patent and that said Letters Patent is hereby corrected as shown below:

On the cover page, under the subheading Related U.S. Application Data, in line 3, please delete "continuation-in-part" and insert --continuation--, therefor.

In column 1, line 2 (Approx.), please delete "APPLICATION" and insert --APPLICATIONS--, therefor.

In column 1, line 24, please delete "rectification" and insert --recalcification--, therefor.

In column 6, line 57, after "36" please insert --.--.

In column 10, line 13, please delete "removal" and insert --removably--, therefor.

In column 12, line 5, please delete "guidwire" and insert --guidewire--, therefor.

In column 12, lines 55-56 (Approx.), after "disclosure" please insert --.--.

In column 14, line 15, please delete "disposed-such" and insert --disposed such--, therefor.

In column 16, line 26, please delete "to. FIGS." and insert --to FIGS.--, therefor.

In column 17, line 19, please delete "thread ably" and insert --threadably--, therefor.

Signed and Sealed this
Twenty-seventh Day of March, 2012

David J. Kappos
*Director of the United States Patent and Trademark Office*